United States Patent
Matsunami

(10) Patent No.: US 11,029,308 B2
(45) Date of Patent: Jun. 8, 2021

(54) METHODS FOR VAPOR DETECTION AND DISCRIMINATION WITH MAMMALIAN ODORANT RECEPTORS EXPRESSED IN HETEROLOGOUS CELLS

(71) Applicant: DUKE UNIVERSITY, Durham, NC (US)

(72) Inventor: Hiro Matsunami, Durham, NC (US)

(73) Assignee: DUKE UNIVERSITY, Durham, NC (US)

( * ) Notice: Subject to any disclaimer, the term of this patent is extended or adjusted under 35 U.S.C. 154(b) by 0 days.

(21) Appl. No.: 16/345,878

(22) PCT Filed: Oct. 27, 2017

(86) PCT No.: PCT/US2017/058797
§ 371 (c)(1),
(2) Date: Apr. 29, 2019

(87) PCT Pub. No.: WO2018/081588
PCT Pub. Date: May 3, 2018

(65) Prior Publication Data
US 2019/0250148 A1  Aug. 15, 2019

Related U.S. Application Data

(60) Provisional application No. 62/413,549, filed on Oct. 27, 2016.

(51) Int. Cl.
*G01N 33/50* (2006.01)
*G01N 33/00* (2006.01)

(52) U.S. Cl.
CPC ..... *G01N 33/5088* (2013.01); *G01N 33/0001* (2013.01)

(58) Field of Classification Search
None
See application file for complete search history.

(56) References Cited

U.S. PATENT DOCUMENTS

| | | |
|---|---|---|
| 7,425,445 B2 | 9/2008 | Matsunami et al. |
| 7,691,592 B2 | 4/2010 | Matsunami et al. |
| 7,838,288 B2 | 11/2010 | Matsunami et al. |
| 2009/0092997 A1 | 4/2009 | Matsunami et al. |
| 2009/0124003 A1 | 5/2009 | Matsunami et al. |
| 2010/0222561 A1 | 9/2010 | Matsunami et al. |
| 2010/0248390 A1 | 9/2010 | Matsunami et al. |
| 2011/0177964 A1 | 7/2011 | Broach et al. |
| 2012/0015841 A1 | 1/2012 | Shekdar et al. |
| 2014/0096590 A1 | 4/2014 | Amin et al. |
| 2015/0005177 A1* | 1/2015 | Pfister ............... G01N 33/5058 506/2 |

FOREIGN PATENT DOCUMENTS

WO   WO 2016/030378   3/2016

OTHER PUBLICATIONS

Kida et al., Vapor detection and discrimination with a panel of odorant receptors, 2018, Nature Communications | (2018)9: 4556 | DOI: 10.1038/s41467-018-06806-w | www.nature.com/naturecommunications, 10 pages. (Year: 2018).*
Sato et al., Chemical Vapor Detection Using a Reconstituted Insect Olfactory Receptor Complex, 2014, Angew. Chem. Int. Ed. 53: 11798-11802 (Year: 2014).*
Zhuang et al., Evaluating cell-surface expression and measuring activation of mammalian odorant receptors in heterologous cells, Aug. 14, 2008, Nature Protocols 3(9):1402-1413 (Year: 2008).*
Martin, F. et al. Elements of Olfactory Reception in Adult *Drosophila melanogaster*. The Anatomical Record. Jul. 31, 2013, vol. 196, pp. 1477-1488.
Milligan, G protein-coupled receptor dimerisation: Molecular basis and relevance to function. Biochim Biophys Acta 1768, 825-835 (Apr. 2007).
Mombaerts, Genes and ligands for odorant, vomeronasal and taste receptors. Nat Rev Neurosci 5, 263-78 (Apr. 2004).
Olender, T. et al. The Human Olfactory Transcriptome. BMC Genomics. 2016, vol. 17; p. 1-18.
Prinster, C. Hague, R. A. Hall, Heterodimerization of g protein-coupled receptors: specificity and functional significance. Pharmacol Rev 57(3), 289-98 (Sep. 1, 2005).
Reed, Signaling pathways in odorant detection. Neuron 8(2), 205-9 (Feb. 1992).
Saito, H. et al. Odor coding by a Mammalian receptor repertoire. Sci Signal 2(60), ra9, pp. 1-28 (2009).
Saito, M. et al., RTP family members induce functional expression of mammalian odorant receptors. Cell 119(5), 679-91 (Nov. 24, 2004).
Shepherd, Discrimination of molecular signals by the olfactory receptor neuron. Neuron 13, 771-90 (Oct. 1994).
Zhuang, H. Matsunami, Synergism of accessory factors in functional expression of mammalian odorant receptors. J Biol Chem 282(20), 15284-93 (May 18, 2007).
Abdalla, et al. AT1-receptor heterodimers show enhanced G-protein activation and altered receptor sequestration. Nature 407, 94-98 (Sep. 7, 2000).
Boekhoff, E. et al., Rapid activation of alternative second messenger pathways in olfactory cilia from rats by different odorants. Embo J 9, 2453-8 (Aug. 1990).
Buck, L. and R. Axel, A novel multigene family may encode odorant receptors: a molecular basis for odor recognition. Cell 65 175-87 (Apr. 5, 1991).
Buck, L.B., Information Coding in the Vertebrate Olfactory System. Annual review of neuroscience 19, 517-44 (1996).

(Continued)

*Primary Examiner* — John D Ulm
(74) *Attorney, Agent, or Firm* — Casimir Jones, SC; Robert A. Goetz

(57) ABSTRACT

The present invention relates to an odorant receptor based odorant sensor system and related methods. In particular, systems and methods are provided permitting detection and discrimination of an odorant molecule in a vapor/gaseous phase using a panel of odorant receptors expressed in heterologous cells.

7 Claims, 12 Drawing Sheets

(56) References Cited

OTHER PUBLICATIONS

Bush et al., Specificity of Olfactory Receptor Interactions with Other G Protein-coupled Receptors. J Biol Chem 282, 19042 (Jun. 29, 2007) (26) :19042-51.
Chabre, M. and le Maire, Monomeric G-protein-coupled receptor as a functional unit. Biochemistry 44, 9395-403 (Jul. 2005).
Eduardo, L. Ric-8B promotes functional expression of odorant recepors. Proc Natl Acad Sci USA 103 (24), 9310-9314 (Jun. 13, 2006).
Ferrer, I. et al. Olfactory Receptors in Non-Chemosensory Organs: The Nervous System in Health and Disease. Frontiers in Aging Neuroscience. Jul. 5, 2016, vol. 8, article 163, 17 pages.
Firestein, How the olfactory system makes sense of scents. Nature 413(6852), 211-8 (2001).
Hague, C. et al., Olfactory receptor surface expression is driven by association with the β2-adrenergic receptor. Proc Natl Acad Sci USA 101, 13672-13676 (Sep. 14, 2004).
Hansen et al., "Lack of Evidence for AT1R/B2R Hetero . . . " J Biol Chem 284, 1831-1839 (Jan. 16, 2009).
International Search Report and Written Opinion, International Patent Application No. PCT/US2017/058797, dated Mar. 26 2018, 22 pages.
Klasen et al., Odorant-stimulated phosphoinositide signaling in mammalian olfactory receptor neurons. Cell Signal 22, 150-157 (Jan. 2010).
Krautwurst, D. et al. Identification of ligands for olfactory receptors by functional expression of a receptor library. Cell 95(7) 917-26 (Dec. 1998).
Lancet N. Ben-Arie, Olfactory receptors. Curr Biol 3(10) 668-74 (Oct. 1, 1993).
Luttrell, Reviews in molecular biology and biotechnology: transmembrane signaling by G protein-coupled receptors. Mol Biotechnol Jul. 2008;39(3):239-64.
Malnic, J. Hirono, T. Sato L. B. Buck Combinatorial receptor codes for odors. Cell 96, 713-23 (Mar. 5, 1999).
Marshall, Heterodimerization of G-protein-coupled receptors in the CNS. Current Opinion in Pharmacology 1, pp. 40-44 (2001).

\* cited by examiner

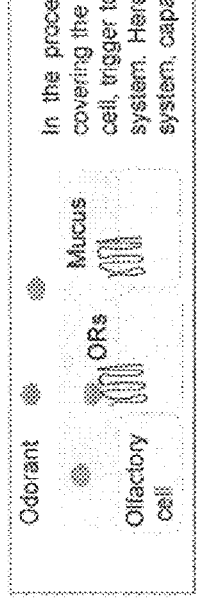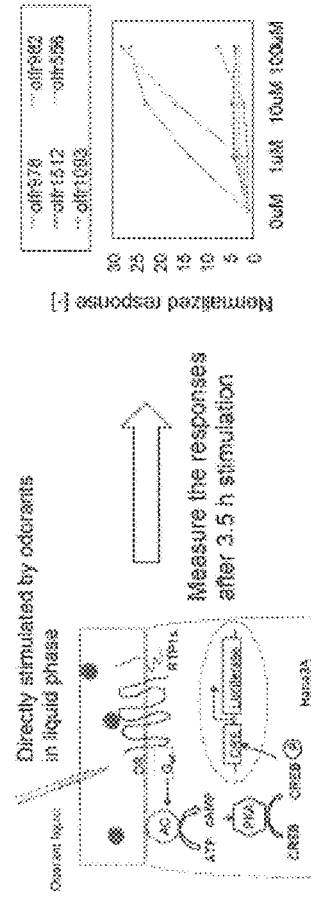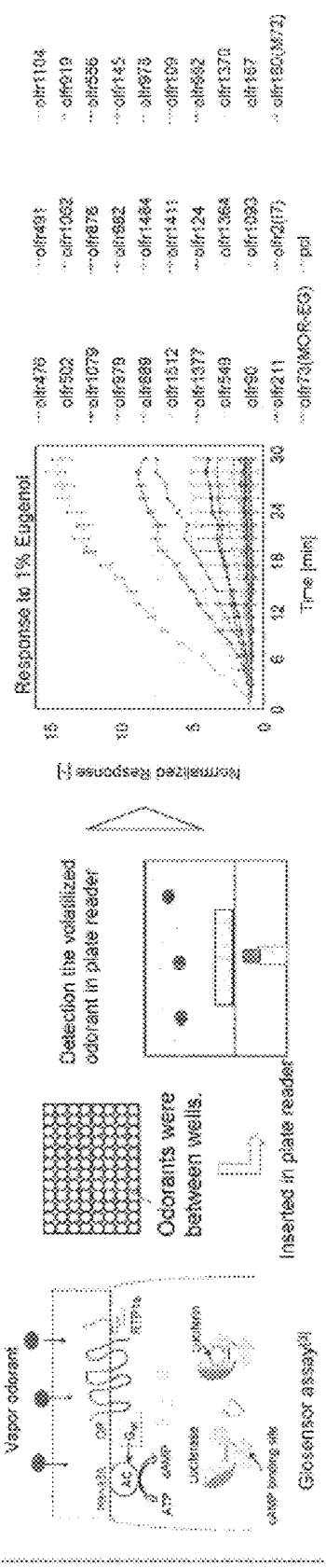
FIG. 1A

METHODS FOR VAPOR DETECTION AND DISCRIMINATION WITH MAMMALIAN ODORANT RECEPTORS EXPRESSED IN HETEROLOGOUS CELLS

CROSS-REFERENCE TO RELATED APPLICATIONS

This application claims priority to U.S. Provisional Patent Application No. 62/413,549, filed Oct. 27, 2016.

STATEMENT REGARDING FEDERALLY SPONSORED RESEARCH OR DEVELOPMENT

This invention was made with Government Support under Federal Grant Nos. DC014423 and DC012095 awarded by the NIH. The Government has certain rights to this invention.

FIELD OF THE INVENTION

The present invention relates to an odorant receptor based odorant sensor system and related methods. In particular, systems and methods are provided permitting detection and discrimination of an odorant molecule in a vapor/gaseous phase using a panel of odorant receptors expressed in heterologous cells.

BACKGROUND

Mammals are capable of detecting and discriminating a large number of volatile chemicals. Fundamentally, this relies on the interaction of odorant molecules and olfactory receptors (ORs), which transduce signals via cAMP-mediated pathways. Previous methods only allow for the measurement of OR-mediated cAMP responses to odorants dissolved in a media. It is desirable for a detection system/methods that allow for the detection of odorants in a vapor phase. Such systems and methods would allow for the measurement of OR activation in more realistic settings, which in turn are useful to screen ligands and antagonists. Further, such systems and methods would be useful as OR-based volatile sensor arrays that could be used to detect specific volatiles, including explosives, solvents for explosives, illegal drugs, spoiled food and malodors.

The present invention addresses this need.

SUMMARY OF THE INVENTION

Experiments conducted during the course of developing embodiments of the present disclosure demonstrated an OR-based odorant sensor system permitting detection and discrimination of an odorant molecule in a vapor/gaseous phase. Within such an OR-based odorant sensor system, it was shown that 1) volatile compound vapors were capable of activating ORs expressed in heterologous cells, 2) each OR demonstrated unique thresholds and dynamic ranges against different odorants, 3) similar odorants were discriminated, and 4) enhanced odorant responses were detected in the presence of odorant binding proteins (OBPs).

Accordingly, the present disclosure relates to an odorant receptor based odorant sensor system and related methods. In particular, systems and methods are provided permitting detection and discrimination of an odorant molecule in a vapor/gaseous phase using a panel of odorant receptors expressed in heterologous cells.

In certain embodiments, the present invention provides methods of identifying at least one odorant receptor responding at least one odorant molecule in a vapor/gaseous phase comprising the steps of:
a) providing a biological sample comprising cells expressing at least one odorant receptor and exposing the biological sample to at least one test compound in a vapor/gaseous phase;
b) measuring a signal that is proportional to activation of one of the odorant receptors in the biological sample, and
c) comparing the measured level of activation of one of the odorant receptors determined in step b) to a reference activation level for the specific odorant receptor determined in the same conditions with a negative control where the biological sample has not been exposed to the at least one test compound in a vapor/gaseous phase.

In certain embodiments, the present invention provides methods of identifying at least one odorant receptor responding at least one odorant molecule in a vapor/gaseous phase comprising the steps of:
a) providing a biological sample comprising cells expressing at least one odorant receptor having been exposed to at least one test compound in a vapor/gaseous phase;
b) measuring a signal that is proportional to activation of one of the odorant receptors in the biological sample, and
c) comparing the measured level of activation of one of the odorant receptors determined in step b) to a reference activation level for the specific odorant receptor determined in the same conditions with a negative control where the biological sample has not been exposed to the at least one test compound in a vapor/gaseous phase.

In such embodiments, when the level of activation determined in step b) in the biological sample after exposure to at least one test compound in a vapor/gaseous phase is higher than the level of activation determined in the same conditions with a negative control without exposure to the test compound in a vapor/gaseous phase, this indicates that said at least one test compound in a vapor/gaseous phase constitutes a ligand acting as an agonist for said at least one odorant receptor.

In such embodiments, when the level of activation determined in step b) in the biological sample after exposure to at least one test compound in a vapor/gaseous phase is lower than the level of activation determined in the same conditions with a negative control without exposure to the test compound in a vapor/gaseous phase, this indicates that said at least one test compound in a vapor/gaseous phase constitutes a ligand acting as an antagonist for said at least one odorant receptor.

Such methods are not limited to specific odorant receptors. Indeed, the odorant receptors can be human, murine, mammalian, and any mixture thereof.

In some embodiments, the one or more odorant receptors is selected from the group consisting of MOR129, MOR103, olfr476, olfr491, olfr1104, olfr502, olfr1062, olfr919, olfr1079, olfr876, olfr556, olfr979, olfr962, olfr145, olfr889, olfr1484, olfr978, olfr1512, olfr1411, olfr109, olfr1377, olfr124, olfr992, olfr549, olfr1364, olfr1370, olfr90, olfr1093, olfr167, olfr211, olfr2(I7), OR-S6, Olfr62, S6/79, S18, S46, S50, MOR23-1, MOR31-4, MOR31-6, MOR32-5 and MOR32-11.

In some embodiments, the one or more odorant receptors is selected from the group consisting of OR10A2, OR13C8, OR2AG2, OR2T8, OR4M2, OR52L1, OR5M3, OR7G2, OR10A3, OR13C9, OR2AJ1, OR2V1, OR4N2, OR52M1, OR5M8, OR7G3, OR10A4, OR13D1, OR2AK2, OR2V2, OR4N4, OR52N1, OR5M9, OR8A1, OR10A5, OR13F1, OR2AP1, OR2W1, OR4N5, OR52N2, OR5P2, OR8B12, OR10A6, OR13G1, OR2AT4, OR2W3, OR4P4, OR52N4, OR5P3, OR8B2, OR10A7, OR13H1, OR2B11, OR2Y1, OR4Q3, OR52N5, OR5R1, OR8B3, OR10AD1, OR13J1, OR2B2, OR2Z1, OR4S1, OR52R1, OR5T1, OR8B4, OR10AG1, OR14I6, OR2B3, OR3A1, OR4S2, OR52W1, OR5T2, OR8B8, OR10C1, OR14A2, OR2B6, OR3A2, OR4X1, OR56A1, OR5T3, OR8D1, OR10D3, OR14C36, OR2C1, OR3A3, OR4X2, OR56A3, OR5V1, OR8D2, OR10G2, OR14I1, OR2C3, OR4A15, OR51A2, OR56A4, OR5W2, OR8D4, OR10G3, OR14J1, OR2D2, OR4A16, OR51A4, OR56B1, OR6A2, OR8G1, OR10G4, OR14K1, OR2D3, OR4A47, OR51A7, OR56B3P, OR6B1, OR8G5, OR10G6, OR1A1, OR2F1, OR4A5, OR51B2, OR56B4, OR6B2, OR8H1, OR10G7, OR1A2, OR2F2, OR4B1, OR51B4, OR5A1, OR6B3, OR8H2, OR10G8, OR1B1, OR2G2, OR4C11, OR51B5, OR5A2, OR6C1, OR8H3, OR10G9, OR1C1, OR2G3, OR4C12, OR51B6, OR5AC2, OR6C2, OR8I2, OR1OH1, OR1D2, OR2G6, OR4C13, OR51D1, OR5AK2, OR6C3, OR8J1, OR10H2, OR1D5, OR2H1, OR4C15, OR51E1, OR5AN1, OR6C4, OR8J3, OR10H3, OR1E1, OR2H2, OR4C16, OR51E2, OR5AP2, OR6C6, OR8K1, OR10H4, OR1E2, OR2J1, OR4C3, OR51F1, OR5AR1, OR6C65, OR8K3, OR1OH5, OR1F1, OR2J2, OR4C46, OR51F2, OR5AS1, OR6C68, OR8K5, OR10J1, OR1G1, OR2J3, OR4C5, OR51G1, OR5AU1, OR6C70, OR8S1, OR10J3, OR1I, OR2K2, OR4C6, OR51G2, OR5B12, OR6C74, OR8U1, OR10J5, OR1J, OR2L13, OR4D1, OR51H1P, OR5B17, OR6C75, OR8U9, OR10K1, OR1J2, OR2L2, OR4D10, OR51I1, OR5B2, OR6C76, OR9A2, OR10K2, OR1J4, OR2L3, OR4D11, OR51I2, OR5B21, OR6F1, OR9A4, OR10P1, OR1K1, OR2L5, OR4D2, OR51L1, OR5B3, OR6J1, OR9G1, OR10Q1, OR1L1, OR2L8, OR4D5, OR51M1, OR5C1, OR6K2, OR9G4, OR1OR2, OR1L3, OR2M2, OR4D6, OR51Q1, OR5D13, OR6K3, OR9G9, OR10S1, OR1L4, OR2M3, OR4D9, OR51S1, OR5D14, OR6K6, OR9I1, OR10T2, OR1L6, OR2M4, OR4E2, OR51T1, OR5D16, OR6M1, OR9K2, OR10V1, OR1L8, OR2M5, OR4F15, OR51V1, OR5D18, OR6N1, OR9Q1, OR10W1, OR1M1, OR2M7, OR4F16, OR52A1, OR5F1, OR6N2, OR9Q2, OR10X1, OR1N1, OR2S2, OR4F17, OR52A5, OR5H1, OR6P1, OR10Z1, OR1N2, OR2T1, OR4F21, OR52B1P, OR5H14, OR6Q1, OR11A1, OR1Q1, OR2T10, OR4F29, OR52B2, OR5H15, OR6S1, OR11G2, OR1S1, OR2T11, OR4F3, OR52B4, OR5H2, OR6T1, OR11H1, OR1S2, OR2T12, OR4F4, OR52B6, OR5H6, OR6V1, OR11H12, OR2A1, OR2T2, OR4F5, OR52D1, OR5I1, OR6X1, OR11H4, OR2A12, OR2T27, OR4F6, OR52E2, OR5J2, OR6Y1, OR11H6, OR2A14, OR2T29, OR4K1, OR52E4, OR5K1, OR7A10, OR11L1, OR2A2, OR2T3, OR4K13, OR52E6, OR5K2, OR7A17, OR12D2, OR2A25, OR2T33, OR4K14, OR52E8, OR5K3, OR7A5, OR12D3, OR2A4, OR2T34, OR4K15, OR52H1, OR5K4, OR7C1, OR13A1, OR2A42, OR2T35, OR4K17, OR52I1, OR5L1, OR7C2, OR13C2, OR2A5, OR2T4, OR4K2, OR52I2, OR5L2, OR7D2, OR13C3, OR2A7, OR2T5, OR4K5, OR52J3, OR5M1, OR7D4, OR13C4, OR2AE1, OR2T6, OR4L1, OR52K1, OR5M10, OR7E24, OR13C5, OR2AG1, OR2T7, OR4M1, OR52K2, OR5M11, OR7G1; and/or any variant thereof.

In some embodiments, the biological sample further expresses one or more proteins known to enhance cell surface localization of the odorant receptors selected from REEP1, RTP1 and RTP2.

In some embodiments, the biological sample further expresses one or more odorant receptor binding proteins selected from Lcn3, Lcn4, Lcn10, Lcn11, OBP1a, OBP1b, and OBP2b.

In some embodiments, the biological sample further expresses one or more metabolic enzymes such as, for example, carboxyl esterase (e.g, Ces1d) (see, FIG. 10). In some embodiments, the metabolic enzyme is expressed in olfactory epithelium.

In some embodiments, the biological sample comprises a tissue from the olfactory system.

In some embodiments, the biological sample comprises heterologous cells.

In some embodiments, a luminometer is used for the step of measuring a signal that is proportional to activation of one of the odorant receptors in the biological sample.

In certain embodiments, the present invention provides devices for detecting the presence of a specific odorant molecule in a vapor/gaseous phase comprising a biological sample comprising cells expressing one or more odorant receptors that are activated upon exposure to the specific odorant molecule in a vapor/gaseous phase.

In some embodiments, the device is a handheld device.

In some embodiments, the device is capable of communicating to a user of the device upon detection of the presence of the specific odorant molecule in a vapor/gaseous phase.

In some embodiments, the specific odorant molecule in a vapor/gaseous phase is characteristic of an explosive, solvent(s) for explosives, illegal substances, spoiled food and/or a malodor.

In some embodiments, the biological sample further expresses one or more proteins known to enhance cell surface localization of the odorant receptors selected from REEP1, RTP1 and RTP2.

In some embodiments, the biological sample further expresses one or more odorant receptor binding proteins selected from Lcn3, Lcn4, Lcn10, Lcn11, OBP1a, OBP1b, and OBP2b.

In some embodiments, the biological sample further expresses one or more metabolic enzymes such as, for example, carboxyl esterase (e.g, Ces1d) (see, FIG. 10). In some embodiments, the metabolic enzyme is expressed in olfactory epithelium.

In some embodiments, the biological sample comprises a tissue from the olfactory system.

In some embodiments, the biological sample comprises heterologous cells.

In some embodiments, a luminometer is used for the step of measuring a signal that is proportional to activation of one of the odorant receptors in the biological sample.

In some embodiments, the one or more odorant receptors that are activated upon exposure to the specific odorant molecule in a vapor/gaseous phase are identified through use of the methods described herein.

In certain embodiments, the present invention provides methods of detecting and discriminating an odorant molecule in the vapor/gaseous phase comprising, consisting of, or consisting essentially of: (a) providing i) a cell comprising an odorant receptor, and ii) at least one odorant molecule, the odorant molecule being in a gaseous phase; (b) exposing the at least one odorant molecule to the cell, and (c) detecting the activity of the odorant receptor on the cell.

In some embodiments, the odorant molecule comprises more than one odorant molecule.

In other embodiments, the detecting comprises a reporting system. In certain embodiments, the reporting agent comprises Glosensor™ Assay.

In another embodiment, the odorant receptor comprises a human odorant receptor.

In another embodiment, the odorant receptor comprises a murine odorant receptor.

In other embodiments, the odorant receptor comprises a synthetic odorant receptor.

In other embodiments, the at least one odorant molecule is exposed in the presence of a reference odor compound previously identified as a ligand for the odorant receptor.

In another embodiment, the odorant molecule comprises a volatile odorant molecule.

In other embodiments, the at least one odorant molecule comprises a mixture of odorant molecules.

In another embodiment, the method further comprises the step of (d) detecting the presence or absence of an odorant receptor ligand based upon the activity.

In certain embodiments, the present invention provides methods for identifying an odorant receptor ligand, comprising:
a) providing
i) a cell comprising one or more odorant receptors, and
ii) a test compound in a vapor/gaseous phase;
b) exposing said test compound in a vapor/gaseous phase to said cell in an in vitro setting; and
c) detecting the activity of said odorant receptor, wherein said detecting comprises detecting a reporting agent.

Yet another aspect of the present disclosure provides all that is disclosed and illustrated herein.

BRIEF DESCRIPTION OF THE DRAWINGS

The foregoing aspects and other features of the disclosure are explained in the following description, taken in connection with the accompanying drawings, herein:

FIG. 1A and FIG. 1B is a schematic showing the method of detecting and discriminating odorants in vapor phase using the Glosensor™ cAMP assay in accordance with one embodiment of the present disclosure.

DEFINITIONS

Figure 1B:
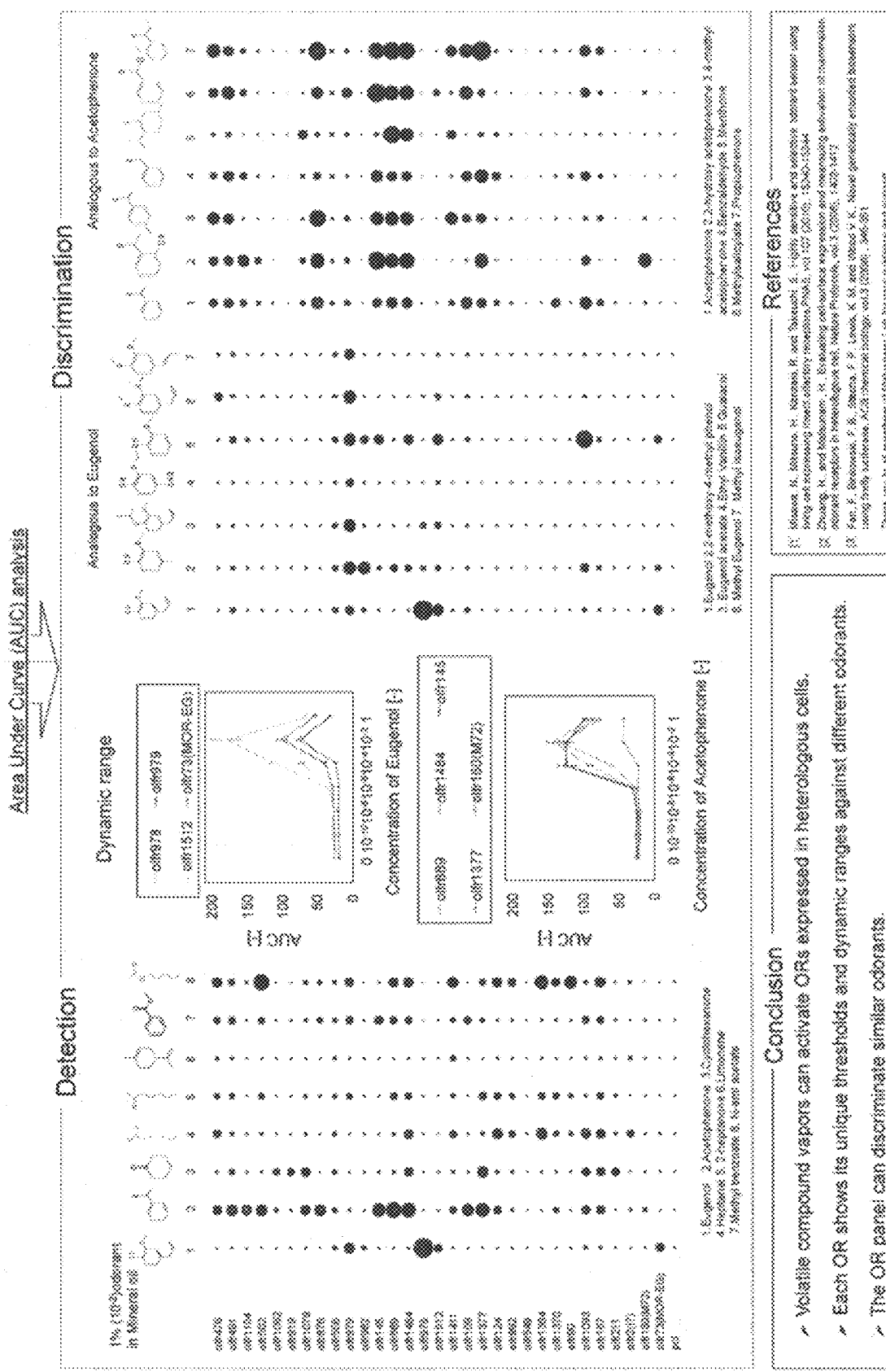

To facilitate understanding of the invention, a number of terms are defined below.

Articles "a" and "an" are used herein to refer to one or to more than one (i.e. at least one) of the grammatical object of the article. By way of example, "an element" means at least one element and can include more than one element.

As used herein, the terms "subject" and "patient" refer to any animal, such as a mammal like a dog, cat, bird, livestock, and preferably a human. Specific examples of "subjects" and "patients" include, but are not limited to, individuals with an olfactory disorder, and individuals with olfactory disorder-related characteristics or symptoms.

As used herewith, "G protein-coupled receptor proteins (GPCRs)", also known as "seven-transmembrane domain receptors", "7TM receptors", "heptahelical receptors", "serpentine receptors", and "G protein-linked receptors (GPLR)", designate a large protein family of receptors that sense molecules outside the cell and activate, inside the cell, signal transductions pathways and, ultimately, cellular responses. GPCRs are found in eukaryotes, including yeast and animals. The ligands that bind and activate these receptors include light-sensitive compounds, odors, pheromones, hormones, and neurotransmitters, and vary in size from small molecules to peptides to large proteins.

As used herewith, the terms "olfactory receptors" designate the receptors expressed in the cell membranes of olfactory sensory neurons responsible for the detection of chemical cues. Activated olfactory receptors are the initial player in a signal transduction cascade which ultimately produces a nerve impulse which is transmitted to the brain. Most of these receptors are members of the GPCR superfamily. The olfactory receptors form a multigene family consisting of about 400 potentially functional genes in humans and about 1250 genes in mice. Olfactory receptors are generally categorized, in mammals, into several receptor families including odorant receptors (ORs), vomeronasal receptors (V1Rs and V2Rs), trace amine-associated receptors (TAARs), formyl peptide receptors (FPRs), and the membrane guanyl cyclase GC-D.

As used herein, the term "odorant receptor" refers to odorant receptors generated from olfactory sensory neurons. Examples of odorant receptors include, but are not limited to, OR-S6, Olfr62, S6/79, S18, S46, S50, MOR23-1, MOR31-4, MOR31-6, MOR32-5 and MOR32-11. Additional examples of odorant receptors (e.g., human) are described in, for example, U.S. Patent Application Publication No. 2017/0052170 and U.S. Patent Application Publication No. 2017/0285009 (each of such odorant receptors described in U.S. Patent Application Publication No. 2017/0052170 and U.S. Patent Application Publication No. 2017/0285009 are herein incorporated by reference in their entireties) (e.g., OR10A1, OR10A3, OR10A4, OR10A5, OR10A6, OR10A7, OR10C1, OR10C2, OR10D4, OR10G2, OR10G3, OR10G4, OR10G7, OR10G8, OR10G9, OR10H1, OR10H2, OR10H3, OR10H4, OR10H5, OR10J1, OR10J3, OR10J5, OR10J6, OR10K1, OR10K2, OR10Q1, OR10R2, OR10S1, OR10T2, OR10V1, OR10Z1, OR11A1, OR11G2, OR11H1, OR11H4, OR11H6, OR11H7P, OR11L1, OR12D3, OR13A1, OR13C2, OR13C3, OR13C4, OR13C5, OR13C7, OR13C8, OR13C9, OR13D1, OR13E2, OR13F1, OR13G1, OR13H1, OR13J1, OR14A16, OR14A2, OR14C36, OR14J1, OR1A1, OR1A2, OR1A2, OR1B1, OR1C1, OR1D2, OR1D4, OR1D5, OR1E1, OR1E2, OR1E2, OR1E5, OR1E5, OR1E6, OR1E7, OR1F1, OR1F10, OR1F11, OR1F12, OR1F2, OR1G1, OR1I1, OR1J1, OR1J2, OR1J2, OR1J4, OR1J5, OR1K1, OR1L1, OR1L3, OR1L4, OR1L6, OR1L8, OR1M1, OR1M1, OR1N1, OR1N2, OR1N3, OR1Q1, OR1S1, OR1S2, OR2A1, OR2A10, OR2A19, OR2A20, OR2A21, OR2A4, OR2A42, OR2A5, OR2A6, OR2A7, OR2AE1, OR2AJ1, OR2AK2, OR2B1, OR2B2, OR2B3, OR2B6, OR2B9, OR2C1, OR2D1, OR2D2, OR2D3, OR2F1, OR2F2, OR2F3, OR2G2, OR2G3, OR2H1, OR2H2, OR2H3, OR2J2, OR2J3, OR2K1, OR2K2, OR2L1, OR2L2, OR2L3, OR2L5, OR2L8, OR2M1, OR2M2, OR2M4, OR2S2, OR2T1, OR2T3, OR2T4, OR2T5, OR2T6, OR2T7, OR2T8, OR2V1, OR2V2, OR2V3, OR2W1, OR2W3, OR2Y1, OR2Z1, OR3A1, OR3A2, OR3A3, OR3A4, OR4A15, OR4A16, OR4A4, OR4A5, OR4B1, OR4C12, OR4C13, OR4C15, OR4C16, OR4C3, OR4C6, OR4D1, OR4D2, OR4D5, OR4D6, OR4D9, OR4E2, OR4F10, OR4F15, OR4F16, OR4F16, OR4F17, OR4F18, OR4F19, OR4F3, OR4F6, OR4K1, OR4K13, OR4K14, OR4K15, OR4K17, OR4K2, OR4K3, OR4K5, OR4L1, OR4M1, OR4M2, OR4N2, OR4N4, OR4N5, OR4P4, OR4Q3, OR4S1, OR4X1, OR4X2, OR51A2, OR51A4, OR51A7, OR51B2, OR51B4, OR51D1, OR51E1, OR51E2, OR51F2, OR51G1, OR51G2, OR51H1, OR51I1, OR51I2, OR51L1, OR51M1, OR51Q1, OR51S1, OR51T1, OR52A1, OR52A2, OR52B2, OR52B4, OR52B4, OR52B4, OR52B6, OR52D1, OR52E2, OR52E4, OR52E5, OR52E6, OR52E8, OR52H1, OR52I1, OR52I2, OR52J3, OR52K1, OR52K2, OR52L1, OR52L2, OR52N1, OR52N2, OR52N4, OR52N5, OR52P1, OR52R1, OR56A4, OR56A6, OR56B2, OR56B4, OR5A1, OR5A2, OR5AC2, OR5AK2, OR5AK3, OR5AN1, OR5AP2, OR5AR1, OR5AS1, OR5AU1, OR5AU1, OR5B13, OR5B16, OR5B17, OR5B2, OR5B3, OR5C1, OR5D13, OR5D14, OR5D16, OR5D18, OR5F1, OR5G3, OR5H1, OR5H2, OR5H6, OR5I1, OR5K1, OR5K2, OR5L1, OR5L2, OR5M1, OR5M10, OR5M11, OR5M11, OR5M3, OR5M3, OR5M8, OR5M9, OR5P2, OR5P3, OR5T2, OR5T3, OR5V1, OR6A1, OR6B1, OR6B2, OR6C1, OR6C2, OR6C3, OR6F1, OR6J2, OR6K3, OR6K6, OR6M1, OR6N1, OR6N2, OR6P1, OR6Q1, OR6S1, OR6T1, OR6V1, OR6X1, OR6Y1, OR7A10, OR7A17, OR7A2, OR7A5, OR7C1, OR7C2, OR7D2, OR7D2, OR7D4P, OR7E102, OR7E120, OR7G1, OR7G2, OR7G3, OR8A1, OR8B12, OR8B2, OR8B3, OR8B4, OR8B8, OR8D1, OR8D2, OR8D4, OR8G1, OR8G2, OR8H1, OR8H2, OR8H3, OR8I2, OR8J1, OR8J3, OR8K1, OR8K3, OR8K5, OR9A2, OR9A4, OR9G1, OR9G4, OR9G5, OR9I1, OR9K2, and OR9Q1 as described in U.S. Patent Application Publication No. 2017/0052170) (e.g., Tables 9 and 10 of U.S. Patent Application Publication No. 2017/0052170) (e.g., OR10A2, OR13C8, OR2AG2, OR2T8, OR4M2, OR52L1, OR5M3, OR7G2, OR10A3, OR13C9, OR2AJ1, OR2V1, OR4N2, OR52M1, OR5M8, OR7G3, OR10A4, OR13D1, OR2AK2, OR2V2, OR4N4, OR52N1, OR5M9, OR8A1, OR10A5, OR13F1, OR2AP1, OR2W1, OR4N5, OR52N2, OR5P2, OR8B12, OR10A6, OR13G1, OR2AT4, OR2W3, OR4P4, OR52N4, OR5P3, OR8B2, OR10A7, OR13H1, OR2B11, OR2Y1, OR4Q3, OR52N5, OR5R1, OR8B3, OR10AD1, OR13J1, OR2B2, OR2Z1, OR4S1, OR52R1, OR5T1, OR8B4, OR10AG1, OR14A16, OR2B3, OR3A1, OR4S2, OR52W1, OR5T2, OR8B8, OR10C1, OR14A2, OR2B6, OR3A2, OR4X1, OR56A1, OR5T3, OR8D1, OR10D3, OR14C36, OR2C1, OR3A3, OR4X2, OR56A3, OR5V1, OR8D2, OR10G2, OR14I1, OR2C3, OR4A15, OR51A2, OR56A4, OR5W2, OR8D4, OR10G3, OR14J1, OR2D2, OR4A16, OR51A4, OR56B1, OR6A2, OR8G1, OR10G4, OR14K1, OR2D3, OR4A47, OR51A7, OR56B3P, OR6B1, OR8G5, OR10G6, OR1A1, OR2F1, OR4A5, OR51B2, OR56B4, OR6B2, OR8H1, OR10G7, OR1A2, OR2F2, OR4B1, OR51B4, OR5A1, OR6B3, OR8H2, OR10G8, OR1B1, OR2G2, OR4C11, OR51B5, OR5A2, OR6C1, OR8H3, OR10G9, OR1C1, OR2G3, OR4C12, OR51B6, OR5AC2, OR6C2, OR8I2, OR1OH1, OR1D2, OR2G6, OR4C13, OR51D1, OR5AK2, OR6C3, OR8J1, OR10H2, OR1D5, OR2H1, OR4C15, OR51E1, OR5AN1, OR6C4, OR8J3, OR10H3, OR1E1, OR2H2, OR4C16, OR51E2, OR5AP2, OR6C6, OR8K1, OR10H4, OR1E2, OR2J1, OR4C3, OR51F1, OR5AR1, OR6C65, OR8K3, OR1OH5, OR1F1, OR2J2, OR4C46, OR51F2, OR5AS1, OR6C68, OR8K5, OR10J1, OR1G1, OR2J3, OR4C5, OR51G1, OR5AU1, OR6C70, OR8S1, OR10J3, OR1I, OR2K2, OR4C6, OR51G2, OR5B12, OR6C74, OR8U1, OR10J5, OR1J, OR2L13, OR4D1, OR51H1P, OR5B17, OR6C75, OR8U9, OR10K1, OR1J2, OR2L2, OR4D10, OR51I1, OR5B2, OR6C76, OR9A2, OR10K2, OR1J4, OR2L3, OR4D11, OR51I2, OR5B21, OR6F1, OR9A4, OR10P1, OR1K1, OR2L5, OR4D2, OR51L1, OR5B3, OR6J1, OR9G1, OR10Q1, OR1L1, OR2L8, OR4D5, OR51M1, OR5C1, OR6K2, OR9G4, OR1OR2, OR1L3, OR2M2, OR4D6, OR51Q1, OR5D13, OR6K3, OR9G9, OR10S1, OR1L4, OR2M3, OR4D9, OR51S1, OR5D14, OR6K6, OR9I1, OR10T2, OR1L6, OR2M4, OR4E2, OR51T1, OR5D16, OR6M1, OR9K2, OR10V1, OR1L8, OR2M5, OR4F15, OR51V1, OR5D18, OR6N1, OR9Q1, OR10W1, OR1M1, OR2M7, OR4F16, OR52A1, OR5F1, OR6N2, OR9Q2, OR10X1, OR1N1, OR2S2, OR4F17, OR52A5, OR5H1, OR6P1, OR10Z1, OR1N2, OR2T1, OR4F21, OR52B1P, OR5H14, OR6Q1, OR11A1, OR1Q1, OR2T10, OR4F29, OR52B2, OR5H15, OR6S1, OR11G2, OR1S1, OR2T11, OR4F3, OR52B4, OR5H2, OR6T1, OR11H1, OR1S2, OR2T12, OR4F4, OR52B6, OR5H6, OR6V1, OR11H12, OR2A1, OR2T2, OR4F5, OR52D1, OR5I1, OR6X1, OR11H4, OR2A12, OR2T27, OR4F6, OR52E2, OR5J2, OR6Y1, OR11H6, OR2A14, OR2T29, OR4K1, OR52E4, OR5K1, OR7A10, OR11L1, OR2A2, OR2T3, OR4K13, OR52E6, OR5K2, OR7A17, OR12D2, OR2A25, OR2T33, OR4K14, OR52E8, OR5K3, OR7A5, OR12D3, OR2A4, OR2T34, OR4K15, OR52H1, OR5K4, OR7C1, OR13A1, OR2A42, OR2T35, OR4K17, OR52I1, OR5L1, OR7C2, OR13C2, OR2A5, OR2T4, OR4K2, OR52I2, OR5L2, OR7D2, OR13C3, OR2A7, OR2T5, OR4K5, OR52J3, OR5M1, OR7D4, OR13C4, OR2AE1, OR2T6, OR4L1, OR52K1, OR5M10, OR7E24, OR13C5, OR2AG1, OR2T7, OR4M1, OR52K2, OR5M11, OR7G1 as described in U.S. Patent Application Publication No. 2017/0285009).

As used herein, the term "odorant receptor cell surface localization" or equivalent terms refer to the molecular transport of an odorant receptor to a cell surface membrane. Examples of cell surface localization include, but are not limited to, localization to cilia at the tip of a dendrite, and localization to an axon terminal.

The term "olfactory stimulus" or "odorant" as used herein comprises any molecule, or group of molecules, volatile or not, aqueous soluble or not, gaseous or not gaseous, that could interact with an olfactory receptor system such as an olfactory receptor in vivo or an olfactory receptor in vitro expressed in a cell or a tissue. The sources and the identity of pleasant and unpleasant odorants are very diverse. Olfactory stimuli can be molecules such as alkanes, esters, linear terpenes, cyclic terpenes, aromatic, amines, alcohols, aldehydes, ketones, lactones, thiols, gases. Examples of olfactory stimuli include unpleasant body odors such as those found in breath (methanethiol, hydrogen sulfide, dimethyl sulfide, etc), on the feet (propanoic acid, isovaleric acid, etc), or on the armpits ((E)-3-methyl-2-hexenoic acid, (S)-3-methyl-3-sulfanylhexan-1-ol, 3-hydroxy-3-methylhexanoic acid, propionic acid, androstenone, etc).

As used herein, the term "odorant receptor functional expression" or equivalent terms, refer to an odorant receptor's ability to interact with an odorant receptor ligand (e.g., an odiferous molecule).

Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

It also is understood that any numerical range recited herein includes all values from the lower value to the upper value. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this application.

DETAILED DESCRIPTION

Odor perception in mammals is a complex process mediated by the activation of ORs expressed at the cilia of millions of olfactory sensory neurons (OSNs) lining the olfactory epithelium (see, e.g., L. Buck, R. Axel, Cell 65, 175 (Apr. 5, 1991); S. Firestein, Nature 413, 211 (2001)). Upon activation by cognate odorants, ORs, which are Class A GPCRs, interact with the stimulatory G protein $G_{\alpha olf}$. Release of $G_{\alpha olf}$ from the βγ subunit then activates type III adenylyl cyclase (ACIII), an enzyme that rapidly catalyzes the cyclization of AMP (see, e.g., L. B. Buck, Annual review of neuroscience 19, 517 (1996); G. M. Shepherd, Neuron 13, 771 (October, 1994); R. R. Reed, Neuron 8, 205 (February, 1992); D. Lancet, N. Ben-Arie, Curr Biol 3, 668 (Oct. 1, 1993)). A rise in cytosolic cAMP triggers the activation of cAMP-gated $Ca^{2+}$ channels, ultimately resulting in membrane depolarization and action-potential generation.

While the above pathways for OR activation has been the established paradigm for OR signalling, others have proposed that some odors activate a secondary signaling pathway that involves the secondary messenger IP3, but the molecular mechanisms through which the IP3 pathway is activated is not well understood (see, e.g., K. Klasen et al., Cell Signal 22, 150 (January); I. Boekhoff, E. Tareilus, J. Strotmann, H. Breer, Embo J 9, 2453 (August, 1990)) and is complicated by the heterogeneity of ORs.

This heterogeneity is part due to existence of a large mammalian OR repertoire: more than 350 human and 1000 mouse ORs have been identified thus far. While much is now known about the ligand specificity of other GPCRs, the odor discrimination and specificity of most ORs remain poorly characterized, despite the fact that mammalian ORs were discovered more than 15 years ago (see, e.g., L. Buck, R. Axel, Cell 65, 175 (Apr. 5, 1991)).

Evidence thus far suggests that odor recognition in mammals depends on complex receptor-ligand interactions that result in the activation of a repertoire of ORs expressed by defined subsets of OSNs (see, e.g., B. Malnic, J. Hirono, T. Sato, L. B. Buck, Cell 96, 713 (Mar. 5, 1999); H. Saito, Q. Chi, H. Zhuang, H. Matsunami, J. D. Mainland, Sci Signal 2, ra9 (2009)). Efforts toward understanding OR-ligand interactions have been impeded by poor OR activation in heterologous cell systems. Several cofactors are now used, in combination, to improve OR activation in heterologous cells (see, e.g., P. Mombaerts, Nat Rev Neurosci 5, 263 (April, 2004); L. E. Von Dannecker, A. F. Mercadante, B. Malnic, Proc Natl Acad Sci USA 103, 9310 (Jun. 13, 2006)). For example, it has been previously demonstrated that coexpressing transmembrane, olfactory-specific Receptor Transporting Proteins RTP1 and RTP2 along with ORs in HEK293T cells significantly increase the functional cell-surface expression of ORs (see, e.g., H. Saito, M. Kubota, R. W. Roberts, Q. Chi, H. Matsunami, Cell 119, 679 (Nov. 24, 2004); H. Zhuang, H. Matsunami, J Biol Chem 282, 15284 (May 18, 2007); U.S. Pat. Nos. 7,425,445, 7,838,288, 7,691,592; U.S. Patent Application Publication Nos. 2010/0222561, 2009/0124003, 2009/0092997). ORs that are N-terminally-tagged with the first 20 amino acids of rhodopsin (Rho-tag) are frequently used in heterologous cells because Rho-tag enhances the membrane targeting of some ORs (see, e.g., D. Krautwurst, K. W. Yau, R. R. Reed, Cell 95, 917 (1998)).

In addition to the accessory factors mentioned above, it has been found that the cell-surface expression of one receptor, OR-M71, can be enhanced when non-OR GPCRs, including the beta2-adrenergic receptor β2AR and purinergic receptor P2Y1, are coexpressed in HEK293 cells. However, this enhancement applies only to OR-M71 and a closely related receptor, but not to other ORs (see, e.g., C. Hague et al., Proc Natl Acad Sci USA 101, 13672 (Sep. 14, 2004); C. F. Bush et al., J Biol Chem 282, 19042 (Jun. 29, 2007)). These findings have led to dramatic improvements in OR activation in vitro, and more importantly, support the idea that ORs do not function alone, but require a number of accessory proteins.

While GPCR heteromerization is not well-understood, such interactions have been shown to be essential for the function of a number of GPCRs through a variety of mechanisms (see, e.g., G. Milligan, Biochim Biophys Acta 1768, 825 (April, 2007); S. C. Prinster, C. Hague, R. A. Hall, Pharmacol Rev 57, 289 (Sep. 1, 2005)). For example, heteromerizaton of $GABA_BR1$ and $GABA_BR2$ is required for the proper trafficking of $GABA_B$ receptors in neurons (see, e.g., F. H. Marshall, Current Opinion in Pharmacology 1, 40 (2001)). In other instances, however, heteromer formation appears to regulate GPCR signaling. For example, heteromerization is required for the reciprocal modulation of beta2-adrenergic receptors β2AR and angiotensin II type 1 AT1 receptors in cardiomyocytes. When β2AR activity is blocked, the AT1 receptor is functionally decoupled from Gq, independent of angiotensin binding. Conversely, when the AT1 receptor is blocked, the β2AR is decoupled from Gs, leading to the loss of downstream cAMP signaling (see, e.g., L. Luttrell, Molecular Biotechnology 39, 239 (2008); L. Barki-Harrington, L. M. Luttrell, H. A. Rockman. (2003), vol. 108, pp. 1611-1618). However, apart from several other accepted examples, the general physiological significance of GPCR heteromers has been debated in some cases (see, e.g., G. Milligan, Biochim Biophys Acta 1768, 825 (April, 2007); M. Chabre, M. le Maire, Biochemistry 44, 9395 (2005); S. AbdAlla, H. Lother, U. Quitterer, Nature 407, 94 (Sep. 7, 2000); J. L. Hansen et al., J Biol Chem 284, 1831 (Jan. 16, 2009)).

As noted, experiments conducted during the course of developing embodiments of the present disclosure demonstrated an OR-based odorant sensor system permitting detection and discrimination of an odorant molecule in a vapor/gaseous phase. Within such an OR-based odorant sensor system, it was shown that 1) volatile compound vapors were capable of activating ORs expressed in heterologous cells, 2) each OR demonstrated unique thresholds and dynamic ranges against different odorants, 3) similar odorants were discriminated, and 4) enhanced odorant responses were detected in the presence of odorant binding proteins (OBPs).

Accordingly, the present invention relates to an odorant receptor based odorant sensor system and related methods. In particular, systems and methods are provided permitting detection and discrimination of an odorant molecule in a vapor/gaseous phase using a panel of odorant receptors expressed in heterologous cells.

The present invention is not limited to specific aspects of the odorant receptor based odorant sensor system and related methods. For example, in some embodiments, the odorant receptor based odorant sensor system includes cells or cell lines expressing one or more odorant receptors wherein such odorant receptors are capable of being activated upon exposure to an odorant molecule being in a vapor/gaseous phase.

In one aspect, the cells and cell lines of the invention are suitable for use in a cell-based assay. Such cells and cell lines provide consistent and reproducible expression of the one or more odorant receptors of interest over time and, thus, are particularly advantageous in such assays.

In some embodiments, the odorant receptor based odorant sensor system and related methods can be used within methods for identifying the presence of a specific odorant molecule in a vapor/gaseous phase through detecting activation of an odorant receptor known to be activated in the presence of the specific odorant.

In some embodiments, the odorant receptor based odorant sensor system and related methods can be used within methods for "deorphanizing" an odorant receptor, i.e. identifying at least one ligand of at least one odorant receptor and, thus, identifying the members of at least one ligand/odorant receptor pair.

The term "ligand" or "chemical stimulus" as used herein refers to a molecule that can bind an odorant receptor and modulate (activate or inhibit) the function of said odorant receptor. It follows that a ligand can modulate the downstream signaling activities of its cognate chemoreceptor (e.g., a GPCR) and/or the global olfactory response in the specific case of an olfactory receptor. When a molecule activates a chemoreceptor (e.g., odorant receptor), it is qualified as "agonist" of said receptor. When a molecule inhibits the activation by an agonist of its cognate chemoreceptor, said molecule is qualified as "antagonist" of said receptor. A ligand for a chemoreceptor (e.g., odorant receptor) can be a molecule of various chemical structures including a peptide, a polypeptide (including an antibody or antigen-binding fragment thereof), a lipid, a carbohydrate, a nucleic acid, a small organic or non-organic molecule including but not limited to an odorant, a fragrance compound and a pheromone, a molecule from a synthetic or natural source, from a chemical or peptide library for instance. A chemical stimulus that can modulate the function of an olfactory receptor is called an "olfactory stimulus".

The terms "agonist" and "antagonist" of a chemoreceptor refer herewith to an agent that modulates (activates and inhibits, respectively) the function of said chemoreceptor and, thus, the downstream signaling activities related to said chemoreceptor and/or, in the case of a ligand binding an olfactory receptor for instance, a global olfactory response related to said olfactory receptor. The agonist and antagonist of a chemoreceptor can act by modulating (enhancing and inhibiting, respectively) the binding of a ligand for its chemoreceptor. Said agonist and said antagonist can be of various natures including a peptide, a polypeptide, an antibody or antigen-binding fragment thereof, a lipid, a carbohydrate, a nucleic acid, a small organic or non-organic molecule including but not limited to an odorant, a fragrance compound and a pheromone, a molecule from a synthetic or natural source, from a chemical or peptide library for instance.

In some embodiments, the invention provides methods of identifying at least one odorant receptor for at least one ligand comprising the steps of:

a) providing a biological sample comprising cells expressing at least one odorant receptor and exposing the biological sample to at least one test compound in a vapor/gaseous phase (e.g., an odorant molecule being in a vapor/gaseous phase);

b) measuring the level of activation of one of the odorant receptors, c) comparing the measured level of activation of one of the odorant receptors determined in step b) to a reference activation level for the specific odorant receptor determined in the same conditions with a negative control where the biological sample has not been exposed to said at least one test compound in a vapor/gaseous phase;

wherein a difference between the level of activation determined in step b) and the level of activation in the same conditions with a negative control indicates that said at least one test compound in a vapor/gaseous phase constitutes a ligand for said at least one odorant receptor and is able to bind and modulate the activity of said at least one odorant receptor.

In some embodiments, the invention provides methods of identifying at least one odorant receptor for at least one ligand comprising the steps of:

a) providing a biological sample comprising cells expressing at least one odorant receptor, wherein said biological sample (i) has been exposed to at least one test compound in a vapor/gaseous phase (e.g., an odorant molecule being in a vapor/gaseous phase);

b) measuring the level of activation of one of the odorant receptors, c) comparing the measured level of activation of one of the odorant receptors determined in step b) to a reference activation level for the specific odorant receptor determined in the same conditions with a negative control where the biological sample has not been exposed to said at least one test compound in a vapor/gaseous phase;

wherein a difference between the level of activation determined in step b) and the level of activation in the same conditions with a negative control indicates that said at least one test compound in a vapor/gaseous phase constitutes a ligand for said at least one odorant receptor and is able to bind and modulate the activity of said at least one odorant receptor.

In such embodiments, when the level of activation determined in step b) in the biological sample after exposure to at least one test compound in a vapor/gaseous phase is higher than the level of activation determined in the same conditions with a negative control without exposure to the test compound in a vapor/gaseous phase, this indicates that said at least one test compound in a vapor/gaseous phase constitutes a ligand acting as an agonist for said at least one odorant receptor.

In such embodiments, when the level of activation determined in step b) in the biological sample after exposure to at least one test compound in a vapor/gaseous phase is lower than the level of activation determined in the same conditions with a negative control without exposure to the test compound in a vapor/gaseous phase, this indicates that said at least one test compound in a vapor/gaseous phase constitutes a ligand acting as an antagonist for said at least one odorant receptor.

In the invention, a biological sample typically comprises isolated cells or cells within a tissue, wherein said cells express at least one odorant receptor and wherein the gene encoding said odorant receptor was naturally present in said cells or was introduced within said cells by genetic engineering. In some embodiments, the biological sample comprises heterologous cells.

The odorant receptor based odorant sensor system is not limited to expressing specific kinds of odorant receptors.

In some embodiments, the odorant receptor based odorant sensor systems express one or more of MOR129, MOR103, olfr476, olfr491, olfr1104, olfr502, olfr1062, olfr919, olfr1079, olfr876, olfr556, olfr979, olfr962, olfr145, olfr889, olfr1484, olfr978, olfr1512, olfr1411, olfr109, olfr1377, olfr124, olfr992, olfr549, olfr1364, olfr1370, olfr90, olfr1093, olfr167, olfr211, and olfr2(I7).

In some embodiments, the odorant receptor based odorant sensor systems express one or more of OR-S6, Olfr62, S6/79, S18, S46, S50, MOR23-1, MOR31-4, MOR31-6, MOR32-5 and MOR32-11.

Examples of human odorant receptors include those listed below, where the reference indicated in brackets provide access to their amino acid sequence and nucleic acid sequence available in public databases:
OR2W1 (ENSG00000229328), OR3A3 (ENSG00000159961), OR5P3 (ENSG00000182334), OR5AN1 (ENSG00000176495), OR11H4 (ENSG00000176198), OR10A3 (ENSG00000170683), OR52I2 (ENSG00000226288), OR7A5 (ENSG00000188269), OR6X1 (ENSG00000221931), OR52I1 (ENSG00000232268), OR4L1 (ENSG00000176246), OR5A2 (ENSG00000172324), OR52B2 (ENSG00000255307), OR4K17 (ENSG00000176230), OR8J1 (ENSG00000262796), OR5P2 (ENSG00000183303), OR56B4 (ENSG00000180919), OR5T3 (ENSG00000261897), OR51D1 (ENSG00000197428), OR6M1 (ENSG00000196099), OR2AG2 (ENSG00000188124), OR8K1 (ENSG00000263328), OR8J1 (ENSG00000172487), OR10K1 (ENSG00000173285), OR4N5 (ENSG00000184394), OR9G4 (ENSG00000262647), OR2H2 (ENSG00000229680), OR4C11 (ENSG00000172188), OR1J4 (ENSG00000239590), OR5T2 (ENSG00000262851), OR4C46 (ENSG00000185926), OR10R2 (ENSG00000198965), OR1N1 (ENSG00000171505), OR5T1 (ENSG00000262784), AC213223.1 (ENSG00000261958), OR1N2 (ENSG00000171501), OR1L8 (ENSG00000171496), OR4M2 (ENSG00000182974), OR5V1 (ENSG00000233046), OR12D2 (ENSG00000235966), OR2W1 (ENSG00000204704), OR4F4 (ENSG00000177693), OR6C75 (ENSG00000187857), OR10W1 (ENSG00000172772), OR2B3 (ENSG00000204703), OR2D3 (ENSG00000178358), OR51L1 (ENSG00000176798), OR8U1 (ENSG00000172199), OR8H2 (ENSG00000181767), OR1K1 (ENSG00000165204), OR7C2 (ENSG00000127529), OR7G3 (ENSG00000170920), OR2AE1 (ENSG00000244623), OR4P4 (ENSG00000181927), OR8K3 (ENSG00000262755), OR4S2 (ENSG00000174982), OR52A5 (ENSG00000171944), OR2Y1 (ENSG00000174339), OR4C6 (ENSG00000181903), OR2V1 (ENSG00000185372), OR8U8 (ENSG00000262315), OR2V2 (ENSG00000182613), OR1D5 (ENSG00000262628), OR2J3 (ENSG00000204701), OR1D2 (ENSG00000184166), OR8K3 (ENSG00000181689), OR4E2 (ENSG00000221977), OR52A1 (ENSG00000182070), OR7D2 (ENSG00000188000), OR13A1 (ENSG00000256574), OR2A42 (ENSG00000212807), OR2A7 (ENSG00000243896), OR4A47 (ENSG00000237388), OR5A1 (ENSG00000172320), OR2J2 (ENSG00000204700), OR8B2 (ENSG00000204293), OR6Y1 (ENSG00000197532), OR6P1 (ENSG00000186440), OR8B3 (ENSG00000196661), OR14J1 (ENSG00000234195), OR10A6 (ENSG00000175393), OR2H1 (ENSG00000204688), OR2W1 (ENSG00000206525), OR8B4 (ENSG00000198657), OR8B8 (ENSG00000197125), OR4D6 (ENSG00000166884), OR8H3 (ENSG00000181761), OR2AG1 (ENSG00000170803), OR56A1 (ENSG00000180934), OR6A2 (ENSG00000184933), OR8J3 (ENSG00000167822), OR8D4 (ENSG00000181518), OR8K5 (ENSG00000181752), OR2A1 (ENSG00000221970), OR1E2 (ENSG00000127780), OR4D5 (ENSG00000171014), OR2F2 (ENSG00000221910), OR2B3 (ENSG00000225736), OR6T1 (ENSG00000181499), OR10S1 (ENSG00000196248), OR10G4 (ENSG00000254737), OR10G9 (ENSG00000236981), OR52J3 (ENSG00000205495), OR10G8 (ENSG00000234560), OR10G7 (ENSG00000182634), OR4K5 (ENSG00000176281), OR10X1 (ENSG00000186400), OR10Z1 (ENSG00000198967), OR5AP2 (ENSG00000172464), OR3A1 (ENSG00000180090), OR3A2 (ENSG00000221882), OR52E2 (ENSG00000176787), OR4K1 (ENSG00000155249), OR2B11 (ENSG00000177535), OR5K2 (ENSG00000231861), OR10C1 (ENSG00000204689), OR5AR1 (ENSG00000172459), OR5R1 (ENSG00000174942), OR10J5 (ENSG00000184155), OR51B6 (ENSG00000176239), OR8B12 (ENSG00000170953), OR8A1 (ENSG00000196119), OR8K1 (ENSG00000150261), OR52D1 (ENSG00000181609), OR1I1 (ENSG00000094661), OR2B3 (ENSG00000206524), OR2C3 (ENSG00000196242), OR14A2 (ENSG00000241128), OR13G1 (ENSG00000197437), OR10A5 (ENSG00000166363), OR6B2 (ENSG00000182083), OR2Z1 (ENSG00000181733), OR9A2 (ENSG00000179468), OR2J3 (ENSG00000206522), OR5M9 (ENSG00000150269), OR6V1 (ENSG00000225781), OR1G1 (ENSG00000183024), OR51B5 (ENSG00000242180), OR9G1 (ENSG00000174914), OR13F1 (ENSG00000186881), OR51Q1 (ENSG00000167360), OR13C4 (ENSG00000148136), OR13C3 (ENSG00000204246), OR6B3 (ENSG00000178586), OR4N4 (ENSG00000183706), OR13C8 (ENSG00000186943), OR51E1 (ENSG00000180785), OR6C65 (ENSG00000205328), OR4F3 (ENSG00000230178), OR7A10 (ENSG00000127515), OR5AC2 (ENSG00000196578), OR5H1 (ENSG00000231192), OR8H1 (ENSG00000262611), OR52N2 (ENSG00000180988), OR52N5 (ENSG00000181009), OR52K2 (ENSG00000181963), OR5B17 (ENSG00000197786), OR5M3 (ENSG00000174937), OR13C5 (ENSG00000277556), OR1F1 (ENSG00000168124), OR52W1 (ENSG00000175485), OR9K2 (ENSG00000170605), OR51M1 (ENSG00000184698), OR52E4 (ENSG00000180974), OR52B6 (ENSG00000187747), OR51B2 (ENSG00000184881), OR52E8 (ENSG00000183269), OR52E6 (ENSG00000205409), OR4F21 (ENSG00000176269), OR52N1 (ENSG00000181001), OR56B1 (ENSG00000181023), OR2F1 (ENSG00000213215), OR12D3 (ENSG00000112462), OR6C76 (ENSG00000185821), OR10C1 (ENSG00000206474), OR12D2 (ENSG00000168787), OR10G2 (ENSG00000255582), OR11H12 (ENSG00000257115), OR5V1 (ENSG00000243729), OR11G2 (ENSG00000196832), OR11A1 (ENSG00000204694), OR1M1 (ENSG00000170929), OR5H14 (ENSG00000236032), OR5J2 (ENSG00000174957), OR1Q1 (ENSG00000165202), OR1B1 (ENSG00000171484), OR7D4 (ENSG00000174667), OR11H1 (ENSG00000130538), OR10V1 (ENSG00000172289), OR52N4 (ENSG00000181074), OR6C70 (ENSG00000184954), OR6C2 (ENSG00000179695), OR1E1 (ENSG00000180016), OR2AP1 (ENSG00000179615), OR6C68 (ENSG00000205327), OR6C4 (ENSG00000179626), OR2J1 (ENSG00000226931), OR51A7 (ENSG00000176895), OR51A4 (ENSG00000205497), OR9G4 (ENSG00000172457), OR51F1 (ENSG00000188069), OR4B1 (ENSG00000175619), OR51G1 (ENSG00000176879), OR51G2 (ENSG00000176893), OR2H2 (ENSG00000204657), OR7A17 (ENSG00000185385), OR10A7 (ENSG00000179919), OR2H2 (ENSG00000206512), OR11H6 (ENSG00000176219), OR6J1 (ENSG00000255804), OR4C13 (ENSG00000258817), OR5AU1 (ENSG00000169327), OR4C12 (ENSG00000221954), OR2J2 (ENSG00000196231), OR51F2 (ENSG00000176925), OR1L1 (ENSG00000173679), OR1L3 (ENSG00000171481), OR51S1 (ENSG00000176922), OR51A2 (ENSG00000205496), OR52R1 (ENSG00000176937), OR8S1 (ENSG00000197376), OR6Q1 (ENSG00000172381), OR9I1 (ENSG00000172377), OR14J1 (ENSG00000237777), OR51H1P (ENSG00000176904), OR14J1 (ENSG00000234100), OR4D10 (ENSG00000254466), OR9Q1 (ENSG00000186509), OR51T1 (ENSG00000176900), OR9A4 (ENSG00000258083), OR4M1 (ENSG00000176299), OR4N2 (ENSG00000176294), OR4Q3 (ENSG00000182652), OR51E2 (ENSG00000167332), OR4A16 (ENSG00000181961), OR51I2 (ENSG00000187918), OR4A15 (ENSG00000181958), OR52H1 (ENSG00000181616), OR5I1 (ENSG00000167359), OR7E24 (ENSG00000237521), OR51V1 (ENSG00000176742), OR13C2 (ENSG00000276119), OR10A2 (ENSG00000170790), OR2J3 (ENSG00000229866), OR6C74 (ENSG00000197706), OR10A4 (ENSG00000170782), OR9Q2 (ENSG00000186513), OR13C9 (ENSG00000136839), OR52K1 (ENSG00000196778), OR4D11 (ENSG00000176200), OR1S2 (ENSG00000197887), OR4D1 (ENSG00000141194), OR5B3 (ENSG00000172769), OR5W2 (ENSG00000187612), OR6B1 (ENSG00000221813), OR5I1 (ENSG00000167825), OR2D2 (ENSG00000166368), OR1S1 (ENSG00000172774), OR4D2 (ENSG00000255713), OR4K15 (ENSG00000169488), OR2K2 (ENSG00000171133), OR2A5 (ENSG00000221836), OR7G2 (ENSG00000170923), OR6K2 (ENSG00000196171), OR2S2 (ENSG00000122718), OR4D9 (ENSG00000172742), OR5D13 (ENSG00000198877), OR5H15 (ENSG00000233412), OR52B4 (ENSG00000221996), OR7G1 (ENSG00000161807), OR10C1 (ENSG00000229412), OR1L4 (ENSG00000136939), OR12D3 (ENSG00000242022), OR10AG1 (ENSG00000174970), OR2A25 (ENSG00000221933), OR5B2 (ENSG00000172365), OR2J1 (ENSG00000204702), OR5K3 (ENSG00000206536), OR6K3 (ENSG00000203757), OR4K14 (ENSG00000169484), OR5H6 (ENSG00000230301), OR10T2 (ENSG00000186306), OR10K2 (ENSG00000180708), OR2AT4 (ENSG00000171561), OR4X2 (ENSG00000172208), OR5K4 (ENSG00000196098), OR5H2 (ENSG00000197938), OR5D14 (ENSG00000186113), OR52M1 (ENSG00000197790), OR12D2 (ENSG00000233481), OR6K6 (ENSG00000180433), OR10J1 (ENSG00000196184), OR4K13 (ENSG00000176253), OR13D1 (ENSG00000179055), OR5D18 (ENSG00000186119), OR4X1 (ENSG00000176567), OR4S1 (ENSG00000176555), OR4C3 (ENSG00000176547), OR4C5 (ENSG00000176540), OR6C6 (ENSG00000188324), OR1J1 (ENSG00000136834), OR4K2 (ENSG00000165762), OR1A2 (ENSG00000172150), OR4F29 (ENSG00000278566), OR2B2 (ENSG00000168131), OR6C1 (ENSG00000205330), OR2A12 (ENSG00000221858), OR2A4 (ENSG00000180658), OR6C3 (ENSG00000205329), OR5F1 (ENSG00000149133), OR1L6 (ENSG00000171459), OR5AS1 (ENSG00000181785), OR5L2 (ENSG00000205030), OR5D16 (ENSG00000205029), OR5C1 (ENSG00000148215), OR56A3 (ENSG00000184478), OR1A1 (ENSG00000172146), OR13H1 (ENSG00000171054), OR2J2 (ENSG00000231676), OR52L1 (ENSG00000183313), OR4F17 (ENSG00000176695), OR2A2 (ENSG00000221989), OR5B12 (ENSG00000172362), OR6S1 (ENSG00000181803), OR56A4 (ENSG00000183389), OR5T2 (ENSG00000181718), OR5T3 (ENSG00000172489), OR5M11 (ENSG00000255223), OR10AD1 (ENSG00000172640), OR4F16 (ENSG00000273547), OR6F1 (ENSG00000169214), OR10D3 (ENSG00000197309), OR5T1 (ENSG00000181698), OR5M10 (ENSG00000254834), OR1C1 (ENSG00000221888), OR14A16 (ENSG00000196772), OR11L1 (ENSG00000197591), OR8H1 (ENSG00000181693), OR2C1 (ENSG00000168158), OR8I2 (ENSG00000172154), OR2W3 (ENSG00000238243), OR2T8 (ENSG00000177462), OR2AJ1 (ENSG00000177275), OR4F15 (ENSG00000182854), OR4F6 (ENSG00000184140), OR8D1 (ENSG00000196341), OR8D2 (ENSG00000197263), OR2L3 (ENSG00000198128), OR10P1 (ENSG00000175398), OR2L13 (ENSG00000196071), OR2L5 (ENSG00000197454), OR2AK2 (ENSG00000187080), OR2L8 (ENSG00000196936), OR1J2 (ENSG00000197233), OR2L2 (ENSG00000203663), OR2M5 (ENSG00000162727), OR2M2 (ENSG00000198601), OR2M3 (ENSG00000228198), OR2M4 (ENSG00000171180), OR2T33 (ENSG00000177212), OR10G3 (ENSG00000169208), OR5M1 (ENSG00000255012), OR2A14 (ENSG00000221938), OR5B21 (ENSG00000198283), OR2T12 (ENSG00000177201), OR4F5 (ENSG00000186092), OR2M7 (ENSG00000177186), OR14C36 (ENSG00000177174), OR6N2 (ENSG00000188340), OR5K1 (ENSG00000232382), OR2T4 (ENSG00000196944), OR2T6 (ENSG00000198104), OR2T1 (ENSG00000175143), OR2T7 (ENSG00000227152), OR2T2 (ENSG00000196240), OR2B6 (ENSG00000124657), OR7C1 (ENSG00000127530), OR2T3 (ENSG00000196539), OR2T5 (ENSG00000203661), OR2G6 (ENSG00000188558), OR2T29 (ENSG00000182783), OR2T34 (ENSG00000183310), OR2T10 (ENSG00000184022), OR2T35 (ENSG00000177151), OR2T27 (ENSG00000187701), OR14I1 (ENSG00000189181), OR4C15 (ENSG00000181939), OR4C16 (ENSG00000181935).

In some embodiments, the odorant receptor is a human odorant receptor, in particular a human odorant receptor selected from the group consisting of: OR10A2, OR13C8, OR2AG2, OR2T8, OR4M2, OR52L1, OR5M3, OR7G2, OR10A3, OR13C9, OR2AJ1, OR2V1, OR4N2, OR52M1, OR5M8, OR7G3, OR10A4, OR13D1, OR2AK2, OR2V2, OR4N4, OR52N1, OR5M9, OR8A1, OR10A5, OR13F1, OR2AP1, OR2W1, OR4N5, OR52N2, OR5P2, OR8B12, OR10A6, OR13G1, OR2AT4, OR2W3, OR4P4, OR52N4, OR5P3, OR8B2, OR10A7, OR13H1, OR2B11, OR2Y1, OR4Q3, OR52N5, OR5R1, OR8B3, OR10AD1, OR13J1, OR2B2, OR2Z1, OR4S1, OR52R1, OR5T1, OR8B4, OR10AG1, OR14A16, OR2B3, OR3A1, OR4S2, OR52W1, OR5T2, OR8B8, OR10C1, OR14A2, OR2B6, OR3A2, OR4X1, OR56A1, OR5T3, OR8D1, OR10D3, OR14C36, OR2C1, OR3A3, OR4X2, OR56A3, OR5V1, OR8D2, OR10G2, OR14I1, OR2C3, OR4A15, OR51A2, OR56A4, OR5W2, OR8D4, OR10G3, OR14J1, OR2D2, OR4A16, OR51A4, OR56B1, OR6A2, OR8G1, OR10G4, OR14K1, OR2D3, OR4A47, OR51A7, OR56B3P, OR6B1, OR8G5, OR10G6, OR1A1, OR2F1, OR4A5, OR51B2, OR56B4, OR6B2, OR8H1, OR10G7, OR1A2, OR2F2, OR4B1, OR51B4, OR5A1, OR6B3, OR8H2, OR10G8, OR1B1, OR2G2, OR4C11, OR51B5, OR5A2, OR6C1, OR8H3, OR10G9, OR1C1, OR2G3, OR4C12, OR51B6, OR5AC2, OR6C2, OR8I2, OR1OH1, OR1D2, OR2G6, OR4C13, OR51D1, OR5AK2, OR6C3, OR8J1, OR10OH2, OR1D5, OR2H1, OR4C15, OR51E1, OR5AN1, OR6C4, OR8J3, OR1OH3, OR1E1, OR2H2, OR4C16, OR51E2, OR5AP2, OR6C6, OR8K1, OR1OH4, OR1E2, OR2J1, OR4C3, OR51F1, OR5AR1, OR6C65, OR8K3, OR1OH5, OR1F1, OR2J2, OR4C46, OR51F2, OR5AS1, OR6C68, OR8K5, OR10J1, OR1G1, OR2J3, OR4C5, OR51G1, OR5AU1, OR6C70, OR8S1, OR10J3, OR1I1, OR2K2, OR4C6, OR51G2, OR5B12, OR6C74, OR8U1, OR10J5, OR1J1, OR2L13, OR4D1, OR51H1P, OR5B17, OR6C75, OR8U9, OR10K1, OR1J2, OR2L2, OR4D10, OR51I1, OR5B2, OR6C76, OR9A2, OR10K2, OR1J4, OR2L3, OR4D11, OR51I2, OR5B21, OR6F1, OR9A4, OR10P1, OR1K1, OR2L5, OR4D2, OR51L1, OR5B3, OR6J1, OR9G1, OR10Q1, OR1L1, OR2L8, OR4D5, OR51M1, OR5C1, OR6K2, OR9G4, OR1OR2, OR1L3, OR2M2, OR4D6, OR51Q1, OR5D13, OR6K3, OR9G9, OR10S1, OR1L4, OR2M3, OR4D9, OR51S1, OR5D14, OR6K6, OR9I1, OR10T2, OR1L6, OR2M4, OR4E2, OR51T1, OR5D16, OR6M1, OR9K2, OR10V1, OR1L8, OR2M5, OR4F15, OR51V1, OR5D18, OR6N1, OR9Q1, OR10W1, OR1M1, OR2M7, OR4F16, OR52A1, OR5F1, OR6N2, OR9Q2, OR10X1, OR1N1, OR2S2, OR4F17, OR52A5, OR5H1, OR6P1, OR10Z1, OR1N2, OR2T1, OR4F21, OR52B1P, OR5H14, OR6Q1, OR11A1, OR1Q1, OR2T10, OR4F29, OR52B2, OR5H15, OR6S1, OR11G2, OR1S1, OR2T11, OR4F3, OR52B4, OR5H2, OR6T1, OR11H1, OR1S2, OR2T12, OR4F4, OR52B6, OR5H6, OR6V1, OR11H12, OR2A1, OR2T2, OR4F5, OR52D1, OR5I1, OR6X1, OR11H4, OR2A12, OR2T27, OR4F6, OR52E2, OR5J2, OR6Y1, OR11H6, OR2A14, OR2T29, OR4K1, OR52E4, OR5K1, OR7A10, OR11L1, OR2A2, OR2T3, OR4K13, OR52E6, OR5K2, OR7A17, OR12D2, OR2A25, OR2T33, OR4K14, OR52E8, OR5K3, OR7A5, OR12D3, OR2A4, OR2T34, OR4K15, OR52H1, OR5K4, OR7C1, OR13A1, OR2A42, OR2T35, OR4K17, OR52I1, OR5L1, OR7C2, OR13C2, OR2A5, OR2T4, OR4K2, OR52I2, OR5L2, OR7D2, OR13C3, OR2A7, OR2T5, OR4K5, OR52J3, OR5M1, OR7D4, OR13C4, OR2AE1, OR2T6, OR4L1, OR52K1, OR5M10, OR7E24, OR13C5, OR2AG1, OR2T7, OR4M1, OR52K2, OR5M11, OR7G1.

In some embodiments, the odorant receptor is a variant of a human odorant receptor, in particular a variant of any one of the human odorant receptors listed above, more particularly a variant having an amino acid sequence having at least 80% identity, for instance at least 85%, at least 90%, at least 95%, at least 96%, at least 97%, at least 98%, or at least 99% identity with the amino acid sequence of a human odorant receptor, in particular with any one of the human odorant receptors listed above.

In some embodiments, the odorant receptor is any type or kind (or variant thereof) of a mammalian odorant receptor (e.g., mouse, canine, human, etc).

In some embodiments, the odorant receptor based odorant sensor systems further express one or more odorant receptor binding proteins. In some embodiments, the one or more odorant receptor binding proteins are selected from Lcn3, Lcn4, Lcn10, Lcn11, OBP1a, OBP1b, and OBP2b.

Figure 10A:
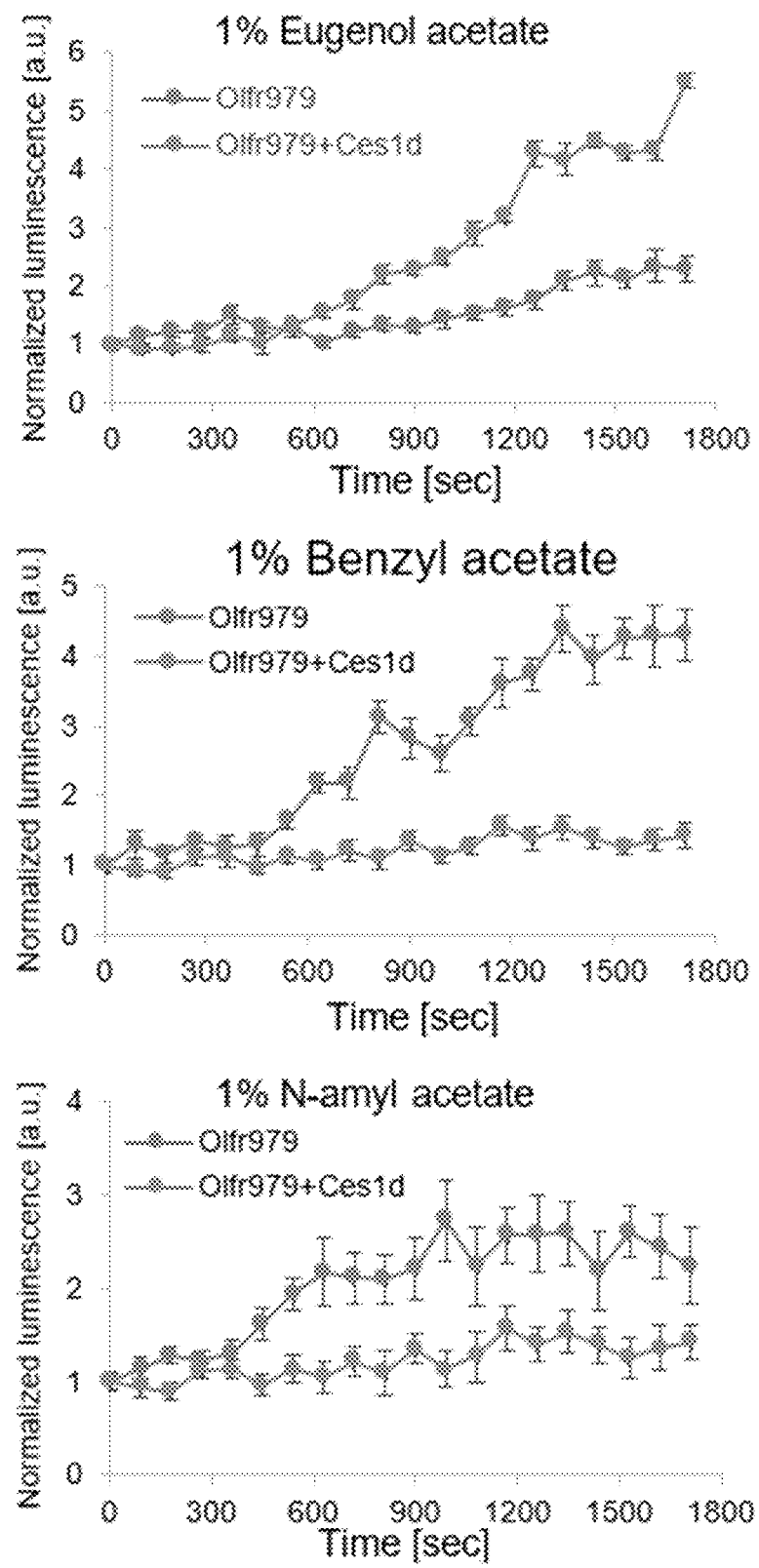
FIG. 10A and FIG. 10B show improved odorant receptor activity when olfactory epithelium expresses a carboxyl esterase (e.g, Ces1d).
Figure 10B:
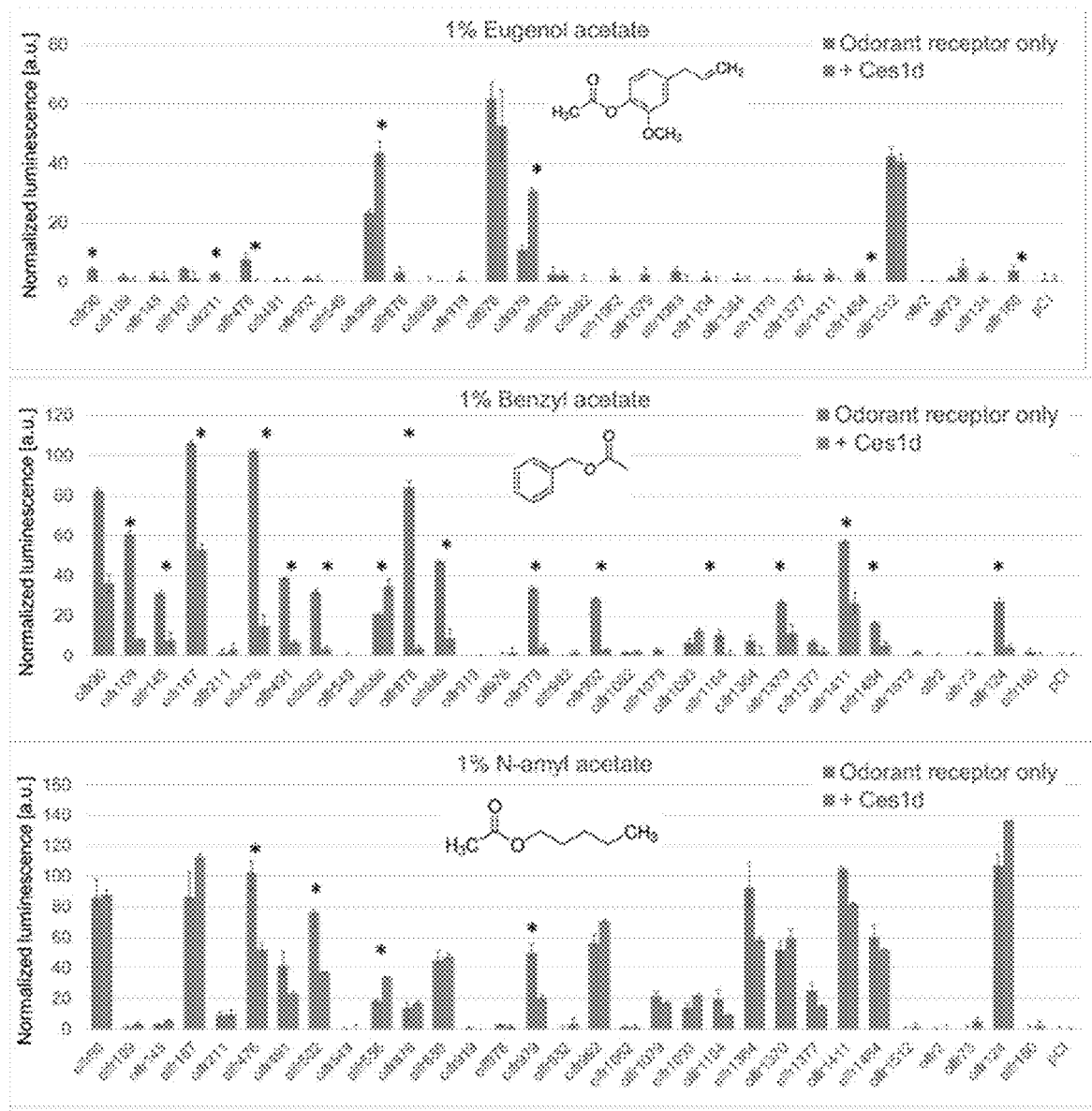

In some embodiments, the odorant receptor based odorant sensor systems further express one or more metabolic enzymes such as, for example, carboxyl esterase (e.g, Ces1d) (see, FIG. 10). In some embodiments, the metabolic enzyme is expressed in olfactory epithelium.

In some embodiments, the odorant receptor based odorant sensor systems further express one or more proteins known to enhance cell surface localization of the odorant receptors. In some embodiments, the one or more proteins known to enhance cell surface localization of the odorant receptors are selected from REEP1, RTP1, and RTP2 (see, e.g., U.S. Pat. No. 7,425,445).

In some embodiments, the biological sample and the gene encoding said odorant receptor are from the same species, e.g. a biological sample from a mouse comprises cells expressing a gene encoding a mouse odorant receptor.

In some embodiments, the biological sample and the gene encoding said odorant receptor are from different species, e.g. a biological sample from a rodent comprises cells expressing a gene encoding a human odorant receptors.

In some embodiments, the biological sample comprises a tissue comprising cells expressing at least one odorant receptor as described above. For example, a tissue suitable for the invention typically comprises olfactory sensory neurons. In a particular embodiment, said tissue is the main olfactory epithelium. Said tissues can be obtained from biopsies of animals (including humans, non-human animals), according to methods known in the art.

In another embodiment, the biological sample used in the invention comprises isolated cells expressing at least one odorant receptor as described above. The cells suitable for the invention are typically isolated from olfactory sensory neurons. The cells suitable for the invention can also be cells from a cell line such as an olfactory sensory neuron cell (e.g., Odora; see, e.g., Murrel and Hunter, 1999, J. Neurosci., 19(19): 8260-70). In a particular embodiment, the cells suitable for the invention are sensory neurons, in particular olfactory sensory neurons isolated from the olfactory system comprising the main olfactory epithelium, vomeronasal organ, septal organ and/or Grueneberg ganglion of an animal. In another embodiment, said olfactory sensory neurons are isolated from the main olfactory epithelium. In a further embodiment, said olfactory sensory neurons are isolated from the vomeronasal organ epithelium. In a further embodiment, said olfactory sensory neurons are isolated from the Grueneberg ganglion. Methods to extract said olfactory sensory neurons are known in the art (see, e.g., Bozza et al., 2002, J. Neuro, 22(8):3033-3043; Riviére et al, Nature 2009 May 28; 459(7246):574-7).

In some embodiments, the cell or cell lines expressing one or more odorant receptors are engineered with Glosensor™. In some embodiments, the cell or cell lines expressing one or more odorant receptors and one or more odorant receptor binding proteins are engineered with Glosensor™.

In some embodiments, the cells or cell lines expressing one or more odorant receptors are placed in an assay plate, such as a 96-well plate or similar type plate, and exposed to the odorant molecule in a vapor/gaseous phase.

Activity of the odorant receptor is then detected when the odorant molecule in a vapor/gaseous phase binds to the receptor ligand. In some embodiments, the detection is determined using the Glosensor™ assay available from Promega Corp. In such an assay, the cAMP pathway is activated upon odor receptor activation, thereby turning on the Glosensor. Cells having actively bound odorant receptors will glow, or be detectable by reading in an appropriate machine, such as a luminometer.

The odorant can be any odorant molecule in a vapor or gas phase.

In some embodiments, the odorant molecule is a volatile odorant molecule, such as an explosive, solvent(s) for explosives, illegal drugs, spoiled food and malodors. In such cases, the odorant receptor based odorant sensor systems can be used as an alert to the presence of such an odorant molecule in any desired setting.

According to the invention, the test compound in a vapor/gaseous phase (e.g., an odorant molecule being in a vapor/gaseous phase) to which the biological sample has been exposed can be of various natures including a peptide, a polypeptide, a lipid, a carbohydrate, and a small organic or non-organic molecule including but not limited to an odorant, a fragrance compound, a pheromone, a molecule from a synthetic or natural source, from a chemical or peptide library for instance.

In a particular embodiment, the test compound in a vapor/gaseous phase is selected from the group consisting of esters, linear terpenes, cyclic terpenes, aromatic, amines, alcohols, aldehydes, ketones, lactones, thiols, sulfated compounds, and alkanes.

In another embodiment, more than one test compound in a vapor/gaseous phase can be tested in a mixture of several test compounds.

The method of the invention is preceded by the exposure of the cells comprised in the biological sample to at least one test compound in a vapor/gaseous phase. Said exposure can be carried out ex vivo, i.e. cells or tissues expressing at least one odorant receptor are exposed to said test compound in a vapor/gaseous phase, or in vivo, i.e. the cells or tissues expressing at least one odorant receptor are from an animal that has been exposed to said test compound.

In general, the method of the invention is preceded by the exposure of the biological sample to the test compound in a vapor/gaseous phase for any amount of time (e.g., less than one second, 1 second, 2 second, 3 seconds, 10 seconds, 30 seconds, 1 minute, 5 minutes, 10 minutes, 30 minutes, an hour, a few hours such as about 5 hours, a day, a month, etc).

In another aspect, the invention provides a vapor/gaseous odorant molecule binding to an odorant receptor, as well as vapor/gaseous agents modulating the binding of a ligand to its odorant receptor, which can be identified by the methods of the invention.

Ligands of at least one odorant receptor and vapor/gaseous agents modulating the binding of a ligand to its odorant receptor, as those identified by the methods according to the invention, are useful for controlling perceived scents. For instance, undesired scents can be blocked, covered or altered by using antagonists of an odorant receptor and desired scents can be enhanced by using a ligand and/or an agonist of an odorant receptor.

Ligands of at least one odorant receptor and agents modulating the binding of a ligand to its odorant receptor, as those identified by the methods according to the invention, are useful in methods of treatment and/or prevention of disorders involving an odorant receptor.

Thus, in certain embodiments, the invention provides compositions comprising at least one odorant molecule in a vapor/gaseous phase of at least one odorant receptor and/or at least one agent modulating the binding of a ligand to its odorant receptor.

The present invention also provides kits for determining detecting and discriminating one or more odorant molecules in a vapor/gaseous phase using a panel of odorant receptors expressed in cells or cell lines (e.g, heterologous cells). The kits are produced in a variety of ways. In some embodiments, the kits contain one or more heterologous cells expressing an odorant receptor of interest. In some embodiments, the kit comprises a panel of heterologous cells each expressing a particular odorant receptor. The kits may also comprise instructions for using the kit. In other embodiments, the kits include ancillary reagents such as buffering agents, cell stabilizing reagents, protein stabilizing reagents, and signal producing systems (e.g., Glosensor™ assay). The test kit may be packaged in any suitable manner, typically with the elements in a single container or various containers as necessary along with a sheet of instructions for carrying out the test. In some embodiments, the kits also preferably include a positive control sample.

Yet another embodiment of the present disclosure provides all that is disclosed and illustrated herein.

One of ordinary skill in the art will readily recognize that the foregoing represents merely a detailed description of certain preferred embodiments of the present invention. Various modifications and alterations of the compositions and methods described above can readily be achieved using expertise available in the art and are within the scope of the invention.

EXAMPLES

The invention, now being generally described, will be more readily understood by reference to the following examples, which are included merely for purposes of illustration of certain aspects and embodiments of the present invention, and are not intended to limit the invention.

Example I

This example describes vapor detection and discrimination with a panel of odorant receptors expressed in heterologous cells.

The method described herein was used to test whether ORs expressed in heterologous cells are activated in vapor phase (see, FIG. 1). In said embodiment, a diverse set of 28 ORs that robustly respond to at least one of the tested odorants, along with three well studied ORs, were selected. Individual ORs were expressed in 96-well plates in triplicates and the responses measured against vapor phase odor stimulation ranging from 10-10 dilution to undiluted odorants using the GloSensor™ assay system. This system was capable of measuring cAMP levels in real time. Significant responses were recorded at concentrations as low as $10^{-6}$ dilution, and robust responses were recorded as low as $10^{-4}$ dilution. Each OR showed a unique response profile to the odorant panel. Lastly, structurally analogous odorants to eugenol and acetophenone were tested. The results showed a discrimination between structural analogs using activation patterns of the set of ORs.

Example II

A comprehensive FACS analysis for a large repertoire of ORs in a heterologous expression system was conducted. Such experiments investigated which ORs are trafficked to cell surface membrane in heterologous cells by carrying out live cell surface staining of HEK293T cells transfected with 244 ORs with an N-terminal Rho tag in the absence of RTP1 and RTP2. In order to quantify the surface staining we performed fluorescence-activated cell sorting (FACS) to measure surface OR levels in these cells. 34 ORs were trafficked to cell surface, which were more than 0.14 fold change. These results indicated ORs are functional without the RTPs.

Figure 2:
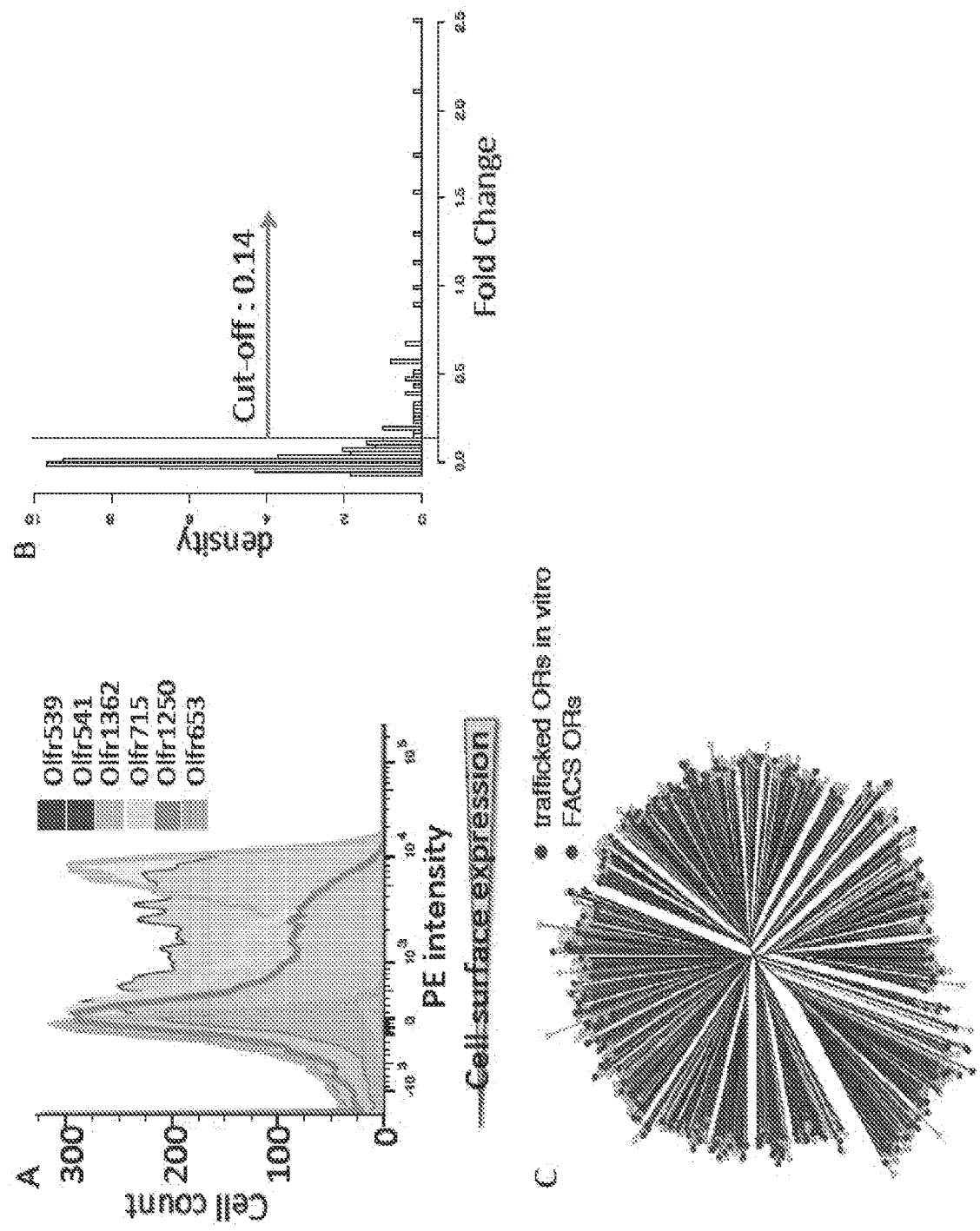
FIG. 2 shows A) FACS results for representative ORs (Olfr539, Olfr541, Olfr1362, Olfr715, Olfr1250 and Olfr653); B) A histogram of FACS results for 244 ORs. Fold changes were calculated using Olfr539, which was greatly trafficked to cell surface, and Olfr541, which was poorly trafficked to cell surface; C) ORs were tested and significantly trafficked ORs were colored in gray-scaled red on a phylogenetic tree of OR amino acid sequences.

FIG. 2 shows A) FACS results for representative ORs (Olfr539, Olfr541, Olfr1362, Olfr715, Olfr1250 and Olfr653); B) A histogram of FACS results for 244 ORs. Fold changes were calculated using Olfr539, which was greatly trafficked to cell surface, and Olfr541, which was poorly trafficked to cell surface; C) ORs were tested and significantly trafficked ORs were colored in gray-scaled red on a phylogenetic tree of OR amino acid sequences.

Example III

This example demonstrates enhanced odorant responses in the presence of odorant binding proteins (OBPs) in the volatile odor-stimulation assays as described herein (see, Example I).

Figure 3:
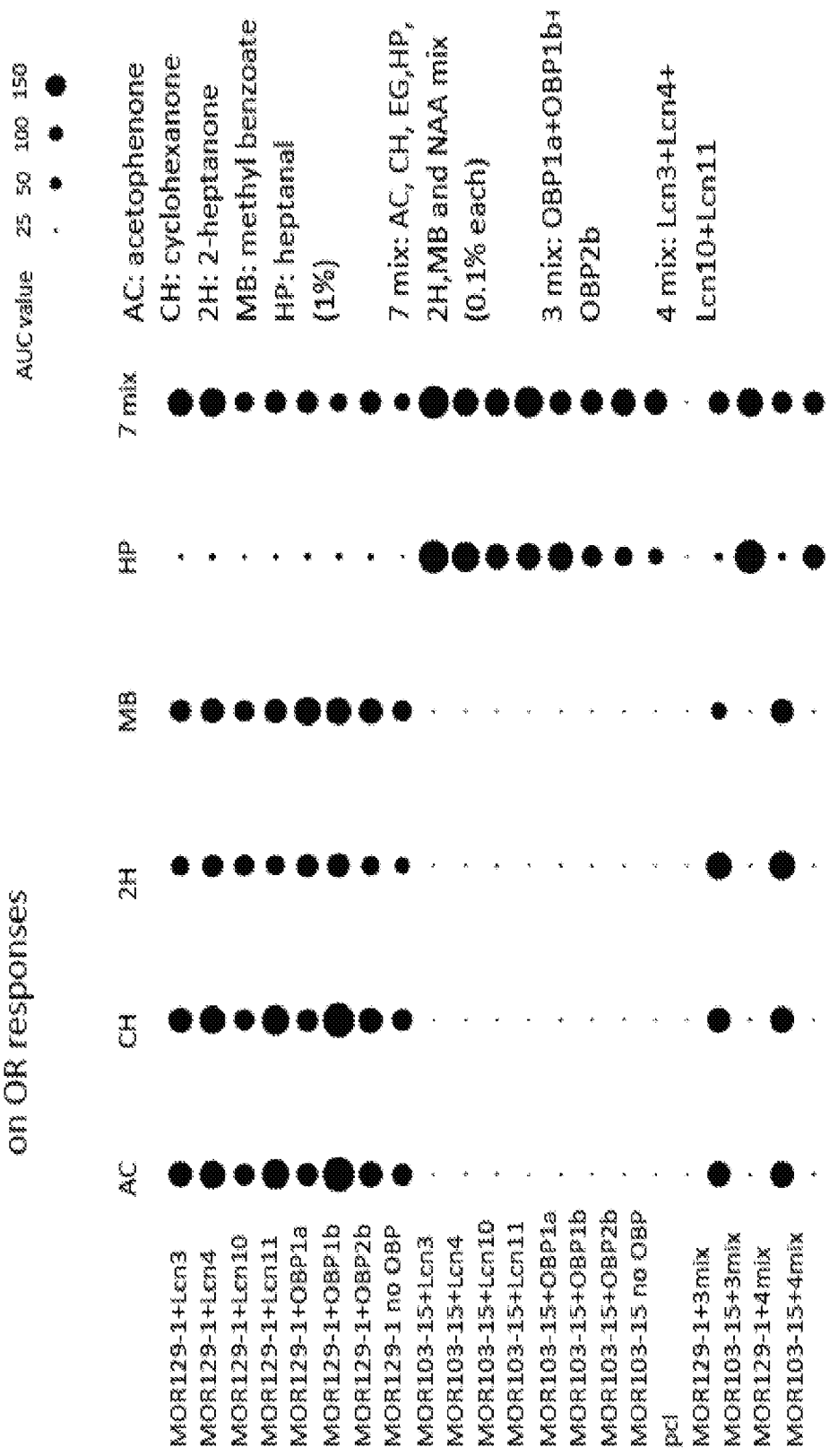
FIG. 3 shows the effect of odorant binding proteins on OR responses in the presence of acetophenone, cyclohexanone, 2-heptanone, methyl benzoate, heptanal, a 7-mixture (a mixture of acetophenone, cyclohexanone, 2-heptanone, methyl benzoate, heptanal, eugenol, and N-amyl acetate).

FIG. 3 shows the effect of odorant binding proteins on OR responses in the presence of acetophenone, cyclohexanone, 2-heptanone, methyl benzoate, heptanal, a 7-mixture (a mixture of acetophenone, cyclohexanone, 2-heptanone, methyl benzoate, heptanal, eugenol, and N-amyl acetate).

Figure 4:
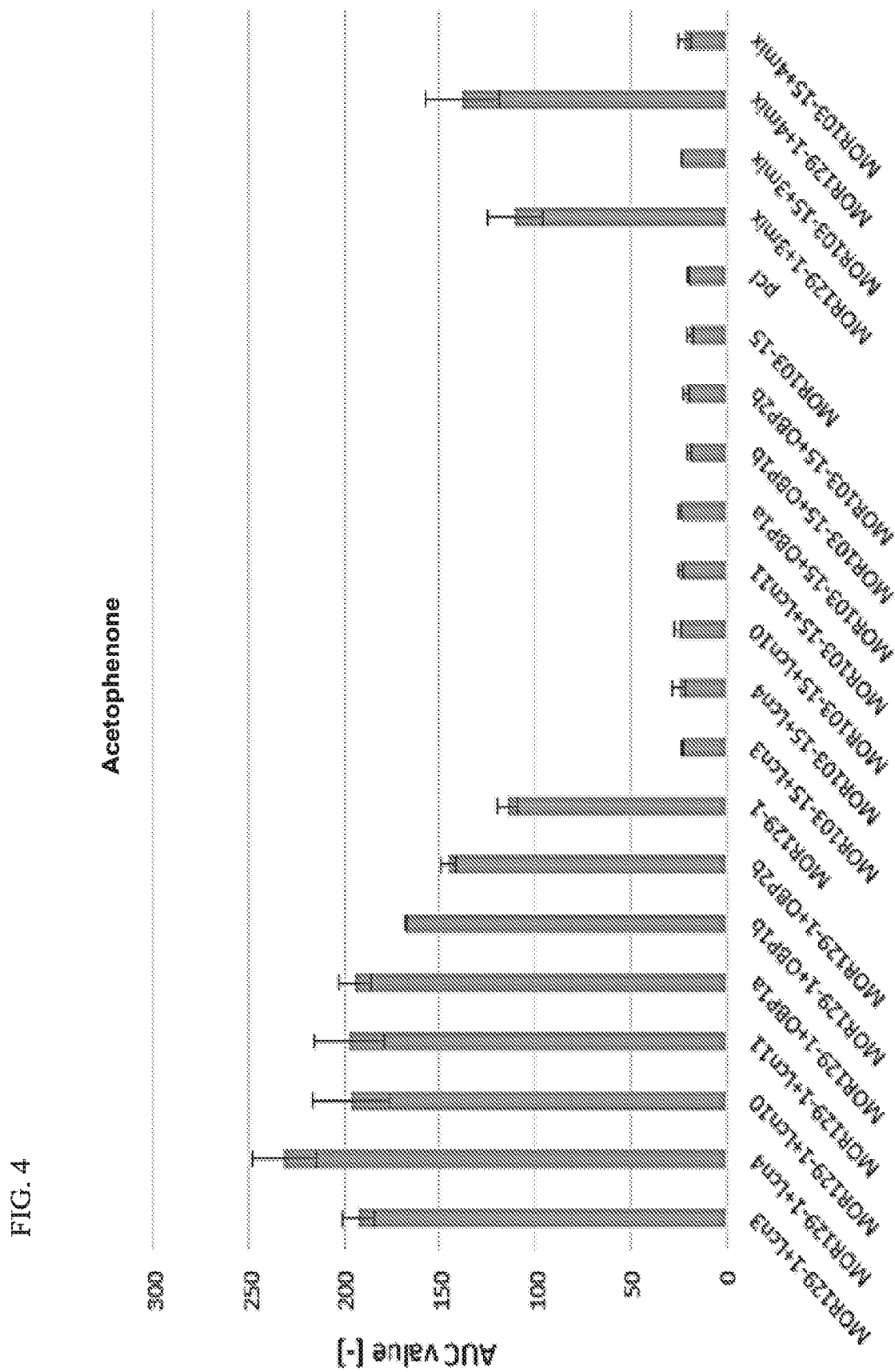
FIG. 4 shows the effect of odorant binding proteins on OR responses in the presence of acetophenone.

FIG. 4 shows the effect of odorant binding proteins on OR responses in the presence of acetophenone.

Figure 5:
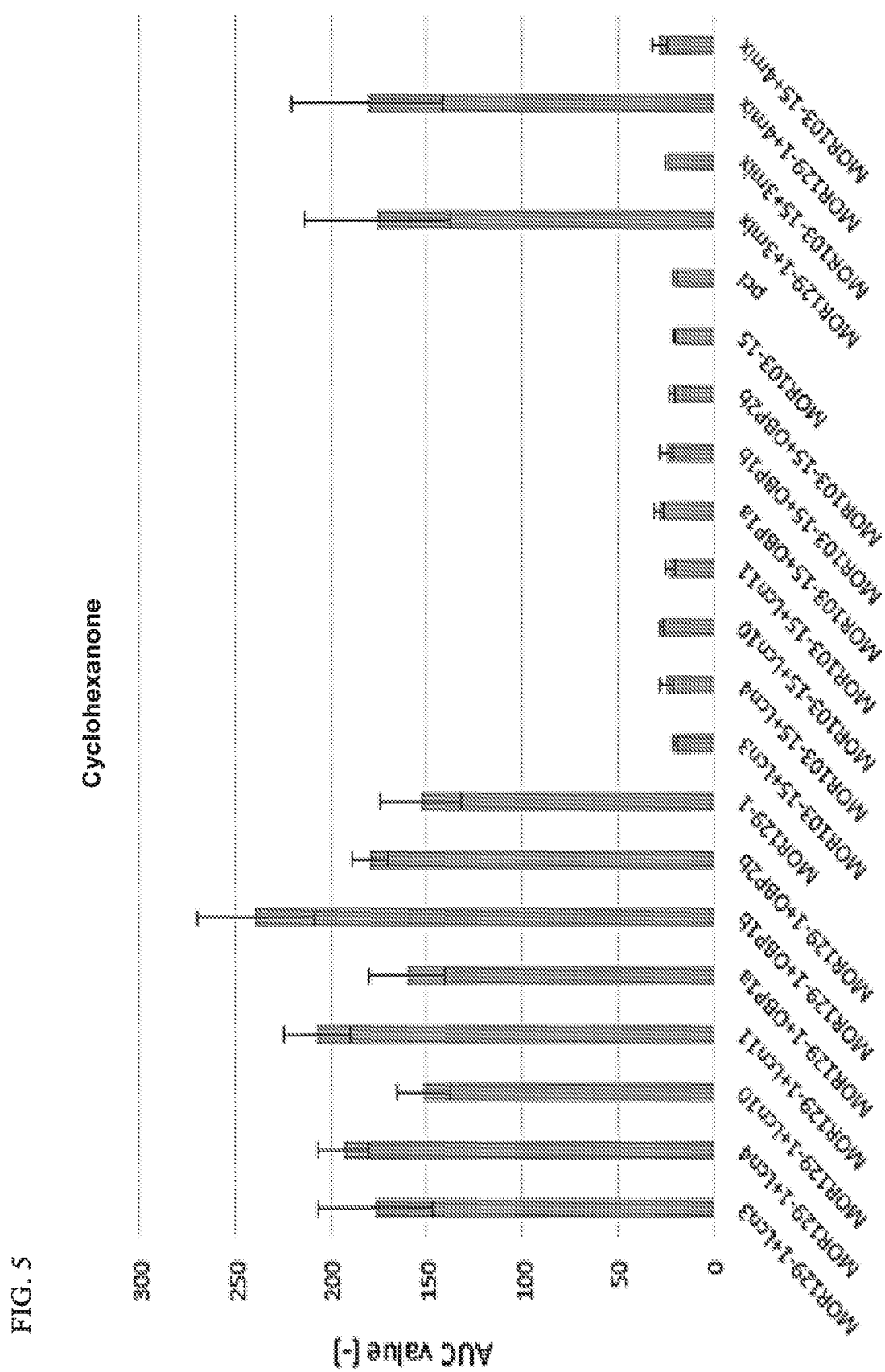
FIG. 5 shows the effect of odorant binding proteins on OR responses in the presence of cyclohexanone.

FIG. 5 shows the effect of odorant binding proteins on OR responses in the presence of cyclohexanone.

Figure 6:
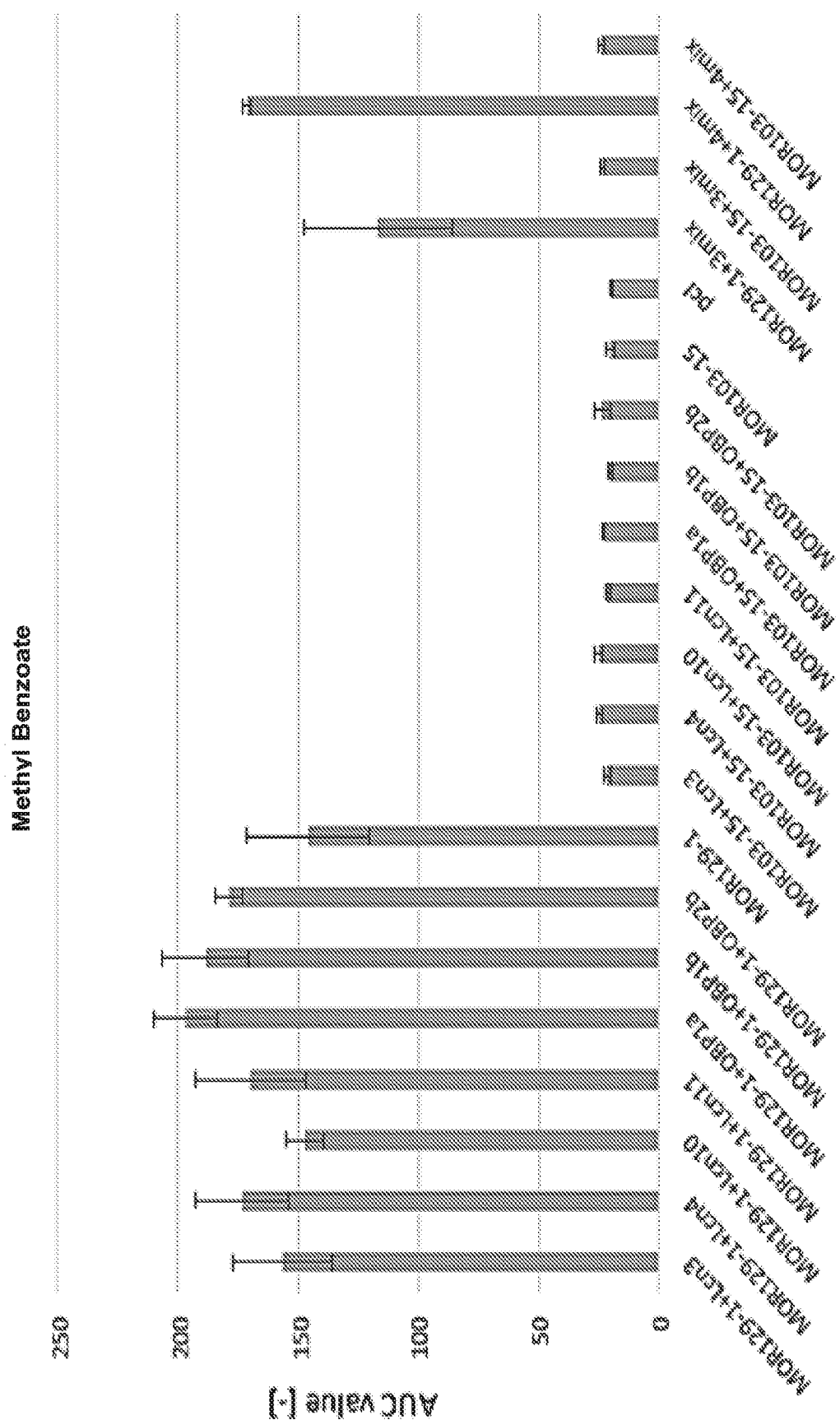
FIG. 6 shows the effect of odorant binding proteins on OR responses in the presence of methyl benzoate.

FIG. 6 shows the effect of odorant binding proteins on OR responses in the presence of methyl benzoate.

Figure 7:
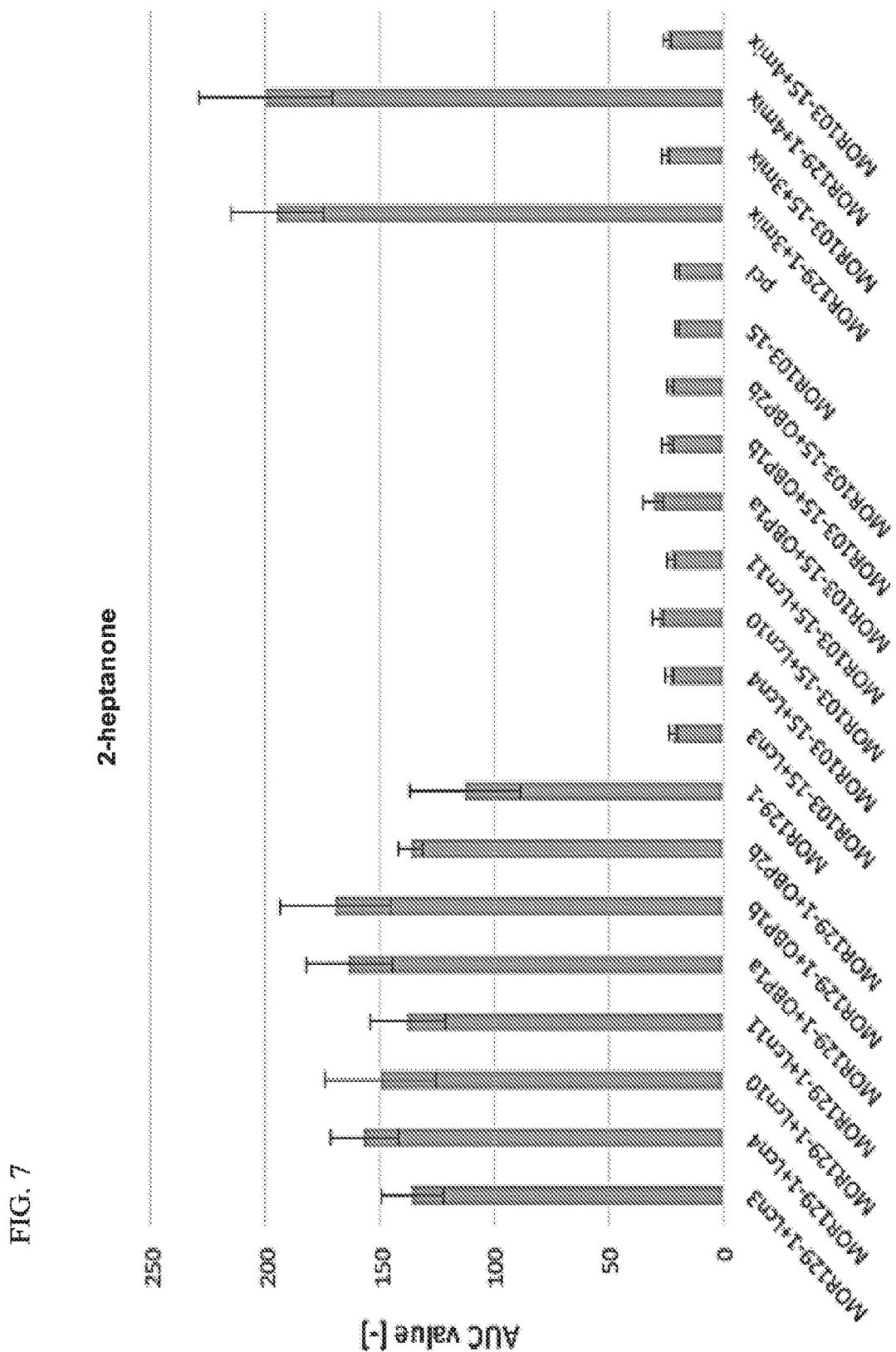
FIG. 7 shows the effect of odorant binding proteins on OR responses in the presence of 2-heptanone.

FIG. 7 shows the effect of odorant binding proteins on OR responses in the presence of 2-heptanone.

Figure 8:
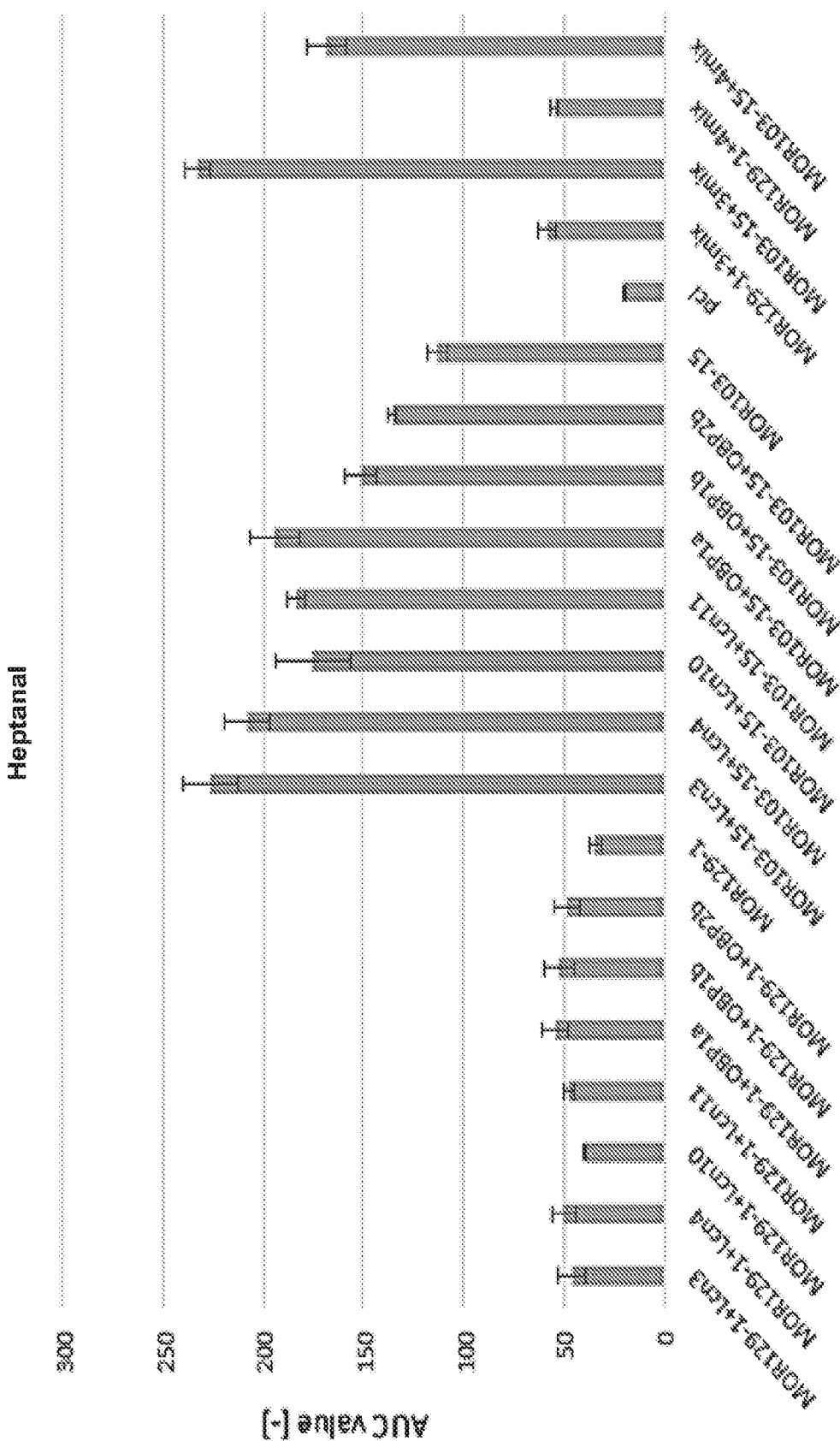
FIG. 8 shows the effect of odorant binding proteins on OR responses in the presence of heptanal.

FIG. 8 shows the effect of odorant binding proteins on OR responses in the presence of heptanal.

Figure 9:
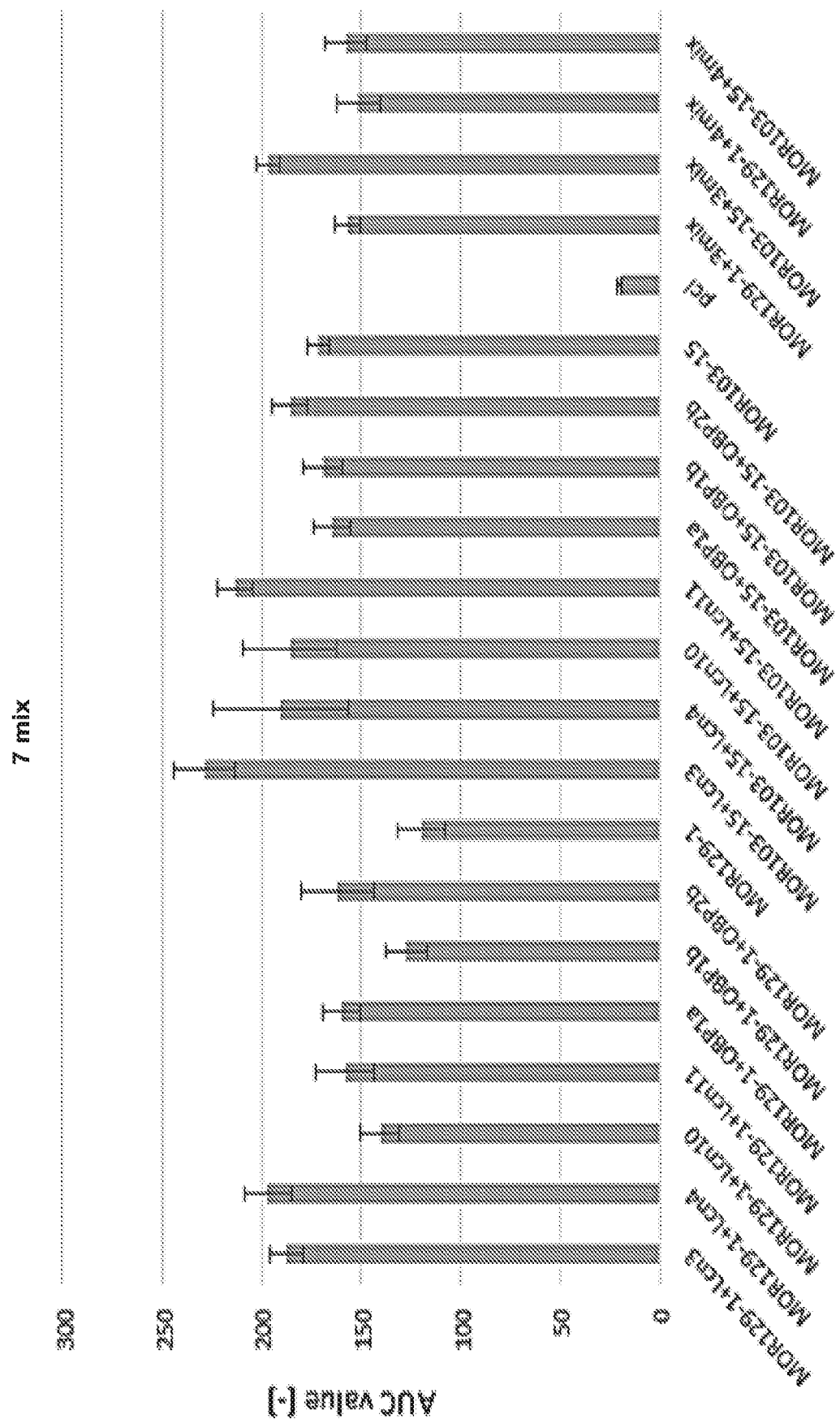
FIG. 9 shows the effect of odorant binding proteins on OR responses in the presence of 7-mixture (a mixture of acetophenone, cyclohexanone, 2-heptanone, methyl benzoate, heptanal, eugenol, and N-amyl acetate).

FIG. 9 shows the effect of odorant binding proteins on OR responses in the presence of 7-mixture (a mixture of acetophenone, cyclohexanone, 2-heptanone, methyl benzoate, heptanal, eugenol, and N-amyl acetate).

Example IV

This example shows the effect of metabolic enzymes to odorants in olfaction.

—Effect of Metabolic Enzymes to Odorants in Olfaction—

Many kinds of proteins, including metabolic enzymes, are expressed in the olfactory epithelium. Some of these proteins are secreted into olfactory mucosa and act in odorant metabolism upstream of OR detection.

Carboxyl Esterase
  catalyzes a chemical reaction breaks carboxylic esters into alcohol and carboxylate.
  expressed in olfactory epithelium (Olson M J et al., J Histochem Cytochem (1993))
  Co-expression of Ces1d which is the most abundant carboxylesterase in olfactory epithelium.

FIG. 10 shows improved odorant receptor activity when olfactory epithelium expresses a carboxyl esterase (e.g, Ces1d).

INCORPORATION BY REFERENCE

The entire disclosure of each of the patent documents and scientific articles referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

I claim:

1. A method of identifying an odorant receptor ligand comprising the steps of:
   a) providing a biological sample comprising cells expressing at least one odorant receptor and exposing the biological sample to at least one test compound in a vapor/gaseous phase,
   wherein the one or more odorant receptors at least includes olfr145, wherein the biological sample further expresses at least one of the following:
one or more proteins known to enhance cell surface localization of the odorant receptors selected from REEP1, RTP1 and RTP2,
one or more odorant receptor binding proteins selected from Lcn3, Lcn4, Lcn10, Lcn11, OBP1a, OBP1b, and OBP2b, and
one or more metabolic enzymes, wherein the one or more metabolic enzymes at least includes carboxyl esterase;
b) measuring a signal that is proportional to activation of one of the odorant receptors in said biological sample, and
c) comparing the measured level of activation of one of the odorant receptors determined in step b) to a reference activation level for the specific odorant receptor determined in the same conditions with a negative control where the biological sample has not been exposed to said at least one test compound in a vapor/gaseous phase.

2. The method of claim 1,
wherein a level of activation determined in step b) in the biological sample after exposure to at least one test compound in a vapor/gaseous phase is higher than the level of activation determined in the same conditions with a negative control without exposure to the test compound in a vapor/gaseous phase indicates that said at least one test compound in a vapor/gaseous phase constitutes a ligand acting as an agonist for said at least one odorant receptor;
wherein a level of activation determined in step b) in the biological sample after exposure to at least one test compound in a vapor/gaseous phase is lower than the level of activation determined in the same conditions with a negative control without exposure to the test compound in a vapor/gaseous phase indicates that said at least one test compound in a vapor/gaseous phase constitutes a ligand acting as an antagonist for said at least one odorant receptor.

3. The method of claim 1, wherein said biological sample comprises a tissue from the olfactory system; and/or wherein the biological sample comprises heterologous cells.

4. The method of claim 1, wherein a luminometer is used for the step of measuring a signal that is proportional to activation of one of the odorant receptors in said biological sample.

5. A method for identifying an odorant receptor ligand, comprising:
a) providing
i) providing a biological sample comprising cells expressing at least one odorant receptor and exposing the biological sample to at least one test compound in a vapor/gaseous phase,
wherein the one or more odorant receptors at least includes olfr145,
wherein the biological sample further expresses at least one of the following:
one or more proteins known to enhance cell surface localization of the odorant receptors selected from REEP1, RTP1 and RTP2,
one or more odorant receptor binding proteins selected from Lcn3, Lcn4, Lcn10, Lcn11, OBP1a, OBP1b, and OBP2b, and
one or more metabolic enzymes, wherein the one or more metabolic enzymes at least includes carboxyl esterase, and
ii) a test compound in a vapor/gaseous phase, wherein said test compound in a vapor/gaseous phase is an odiferous molecule;
b) exposing said test compound in a vapor/gaseous phase to said biological sample in an in vitro setting; and
c) detecting the activity of said odorant receptor, wherein said detecting comprises detecting a reporting agent.

6. The method of claim 5, wherein one or more of said odorant receptors is a human odorant receptor, a murine odorant receptor, or a synthetic odorant receptor.

7. The method of claim 5, further comprising the step of d) detecting the presence or absence of an odorant receptor ligand based upon said activity.

* * * * *